(12) United States Patent
Cho et al.

(10) Patent No.: US 12,163,170 B2
(45) Date of Patent: Dec. 10, 2024

(54) MICROORGANISM WITH INCREASED CARBON MONOXIDE AVAILABILITY AND 2,3-BDO PRODUCTION USING THE SAME

(71) Applicant: KOREA ADVANCED INSTITUTE OF SCIENCE AND TECHNOLOGY, Daejeon (KR)

(72) Inventors: Byung-Kwan Cho, Daejeon (KR); Sangrak Jin, Daejeon (KR); Seulgi Kang, Daejeon (KR); Jiyun Bae, Daejeon (KR); Hyeonsik Lee, Daejeon (KR)

(73) Assignee: KOREA ADVANCED INSTITUTE OF SCIENCE AND TECHNOLOGY, Daejeon (KR)

(\*) Notice: Subject to any disclaimer, the term of this patent is extended or adjusted under 35 U.S.C. 154(b) by 0 days.

(21) Appl. No.: 18/045,822

(22) Filed: Oct. 11, 2022

(65) Prior Publication Data
US 2024/0060065 A1 Feb. 22, 2024

(30) Foreign Application Priority Data
Aug. 16, 2022 (KR) .................. 10-2022-0102140

(51) Int. Cl.
*C12N 9/00* (2006.01)
*C12N 1/20* (2006.01)

(52) U.S. Cl.
CPC .............. *C12N 9/93* (2013.01); *C12N 1/20* (2013.01); *C12Y 602/01001* (2013.01)

(58) Field of Classification Search
CPC ..... C12N 9/93; C12N 1/20; C12Y 602/01001
See application file for complete search history.

(56) References Cited

U.S. PATENT DOCUMENTS

2013/0330809 A1\* 12/2013 Mueller ......... C12Y 101/01004
435/320.1

OTHER PUBLICATIONS

Renna, Maria Catherine, et al. "Regulation of the Bacillus subtilis alsS, alsD, and alsR genes involved in post-exponential-phase production of acetoin." Journal of bacteriology 175.12 (1993): 3863-3875. (Year: 1993).\*
Chang, In Seop, et al. "Effect of CO partial pressure on cell-recycled continuous CO fermentation by Eubacterium limosum KIST612." Process Biochemistry 37.4 (2001): 411-421. (Year: 2001).\*
Roh, Hanseong, et al. "Complete genome sequence of a carbon monoxide-utilizing acetogen, Eubacterium limosum KIST612." Journal of bacteriology 193.1 (2011): 307-308. (Year: 2011).\*
Köpke, Michael, et al. "2, 3-Butanediol production by acetogenic bacteria, an alternative route to chemical synthesis, using industrial waste gas." Applied and environmental microbiology 77.15 (2011): 5467-5475. (Year: 2011).\*
GenBank ADO38273.1; https://www.ncbi.nlm.nih.gov/protein/ADO38273.1; accessed Sep. 7, 2023 (Year: 2018).\*
GenBank ADO38617.1; https://www.ncbi.nlm.nih.gov/protein/ADO38617.1; accessed Sep. 7, 2023 (Year: 2018).\*

(Continued)

*Primary Examiner* — Louise W Humphrey
*Assistant Examiner* — Candice Lee Swift
(74) *Attorney, Agent, or Firm* — Parker Highlander PLLC

(57) ABSTRACT

The present invention relates to a microorganism with increased carbon monoxide availability and use thereof.

13 Claims, 12 Drawing Sheets

Specification includes a Sequence Listing.

(56) References Cited

OTHER PUBLICATIONS

Kim, Ji-Yeon, et al. "Genome-Based Reclassification of Strain KIST612, Previously Classified as Eubacterium limosum, into a New Strain of Eubacterium callanderi." Journal of Microbiology and Biotechnology 33.8 (2023): 1084. (Year: 2023).*

UniProt; https://www.uniprot.org/uniprotkb/E3GG19/entry; accessed Sep. 8, 2023 (Year: 2011).*

Coben SE, Can M, Wittenborn EC, Hendrickson RA, Ragsdale SW, Drennan CL. Crystallographic Characterization of the Carbonylated A-Cluster in Carbon Monoxide Debydrogenase/Acetyl-CoA Synthase. ACS Catal. Sep. 4, 2020;10(17):9741-9746.

Choe D, Szubin R, Poudel S, Sastry A, Song Y, Lee Y, Cho S, Palsson B, Cho BK. RiboRid: A low cost, advanced, and ultra-efficient method to remove ribosomal RNA for bacterial transcriptomics. PLoS Genet. Sep. 27, 2021;17(9).

Drake HL, Gössner AS, Daniel SL. Old acetogens, new light. Ann N Y Acad Sci. Mar. 2008;1125:100-28.

Shin J, Kang S, Song Y, Jin S, Lee JS, Lee JK, Kim DR, Kim SC, Cho S, Cho BK. Genome Engineering of *Eubacterium limosum* Using Expanded Genetic Tools and the CRISPR-Cas9 System. ACS Synth Biol. Sep. 20, 2019;8(9):2059-2068.

Kang S, Song Y, Jin S, Shin J, Bae J, Kim DR, Lee JK, Kim SC, Cho S, Cho BK. Adaptive Laboratory Evolution of *Eubacterium limosum* ATCC 8486 on Carbon Monoxide. Front Microbiol. Mar. 11, 2020;11:402.

Love MI, Huber W. Anders S. Moderated estimation of fold change and dispersion for RNA-seq data with DESeq2. Genome Biol. 2014;15(12):550.

\* cited by examiner

[FIGS. 1A-1E]
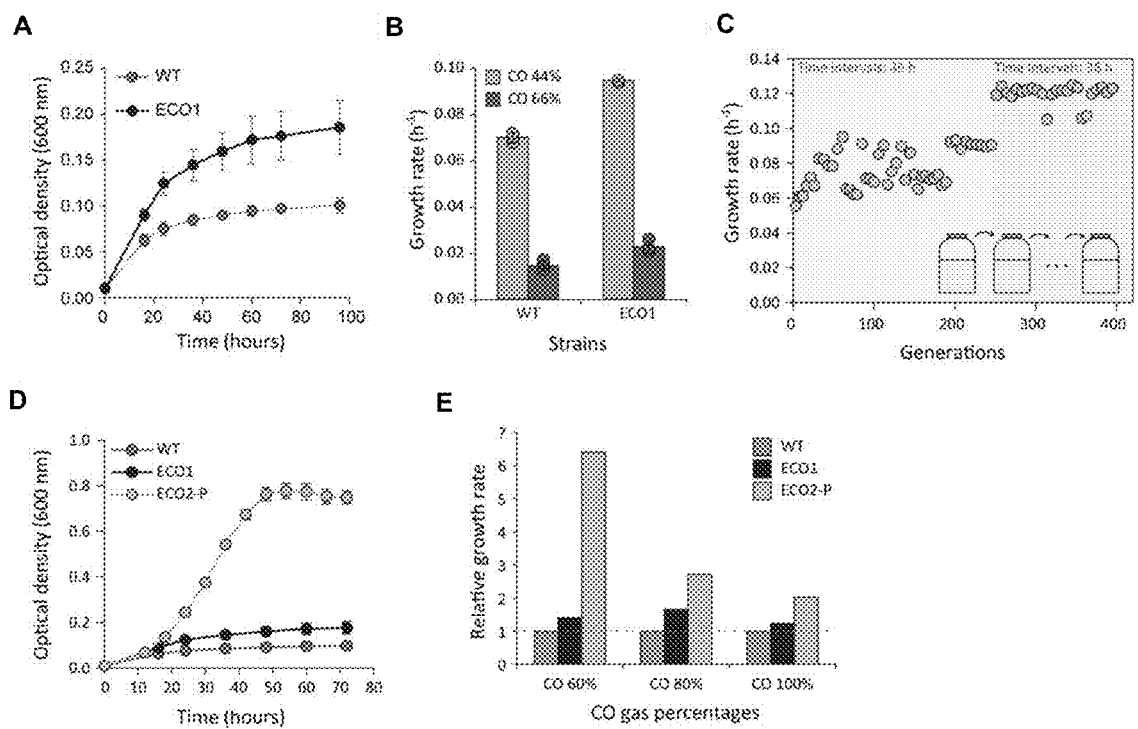

[FIGS. 2A-2B]
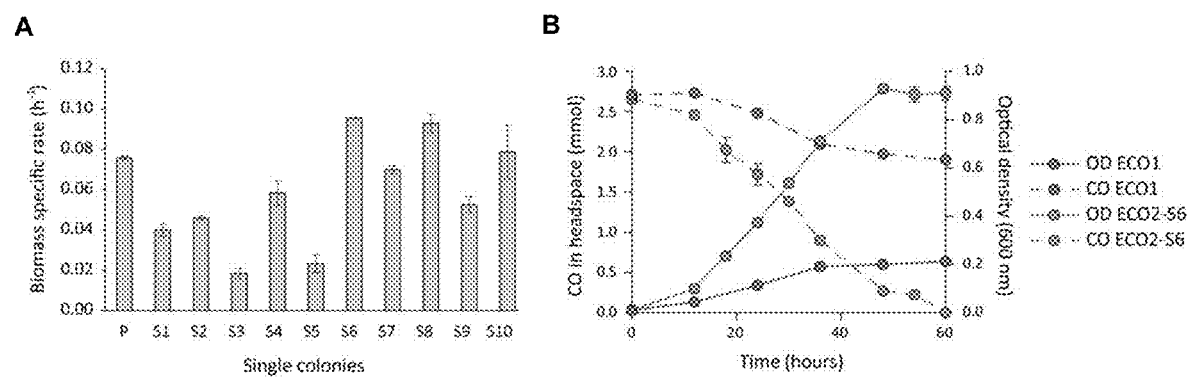

[FIGS. 3A-3D]
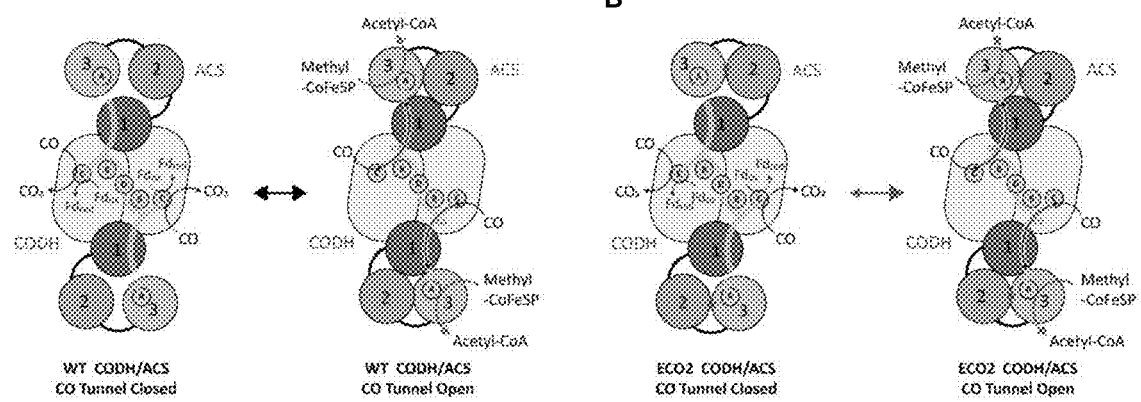
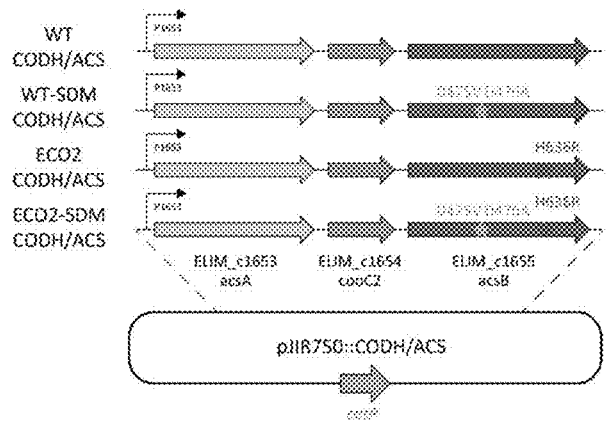
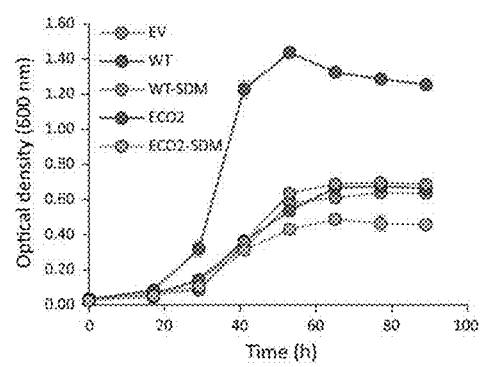

[FIGS. 4A-4B]
A 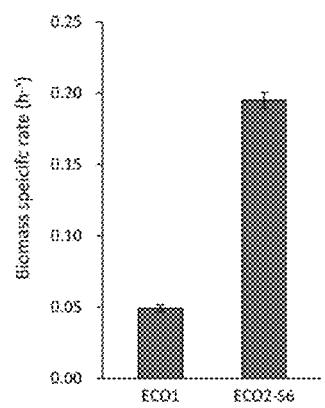
B 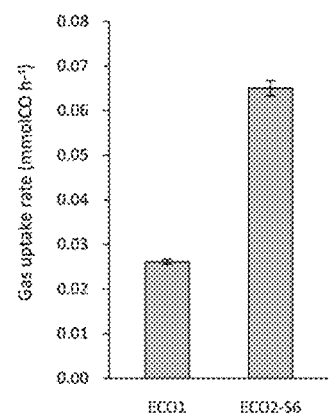

[FIGS. 5A-5C]
A
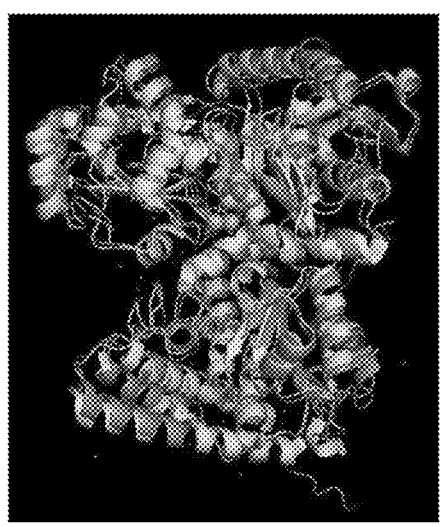
B
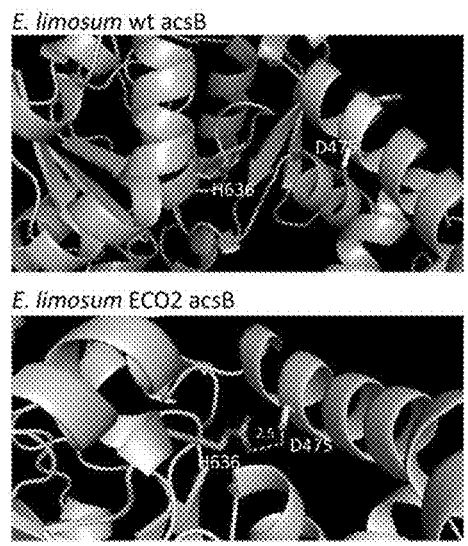
C
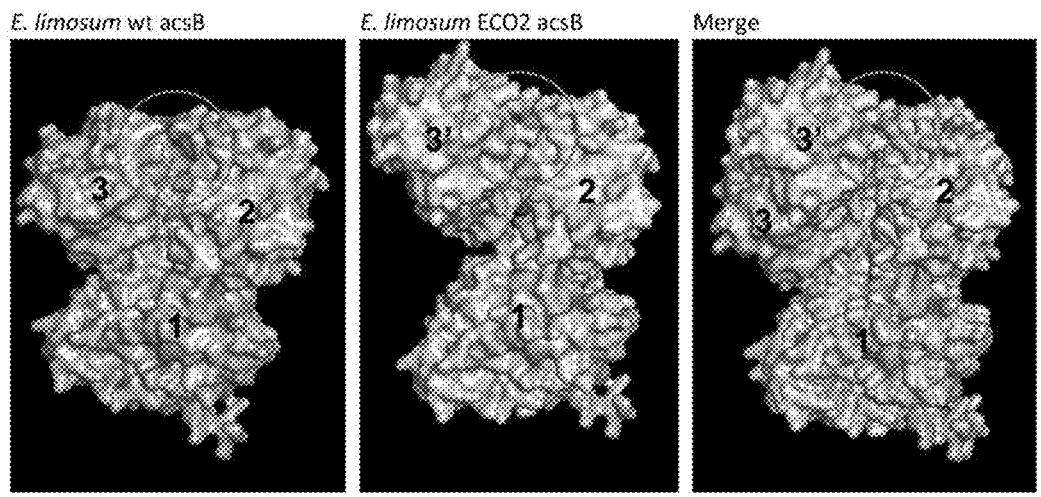

[FIGS. 6A-6B]
A
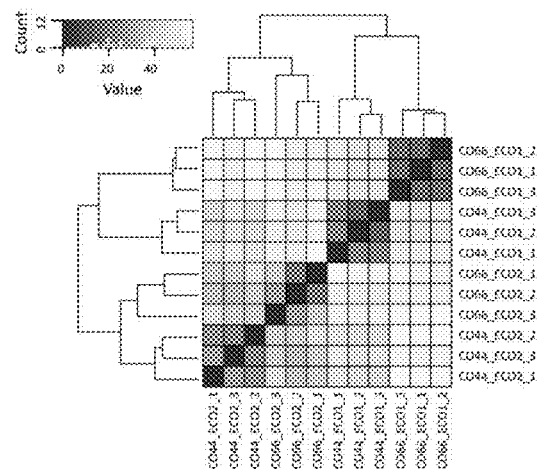
B
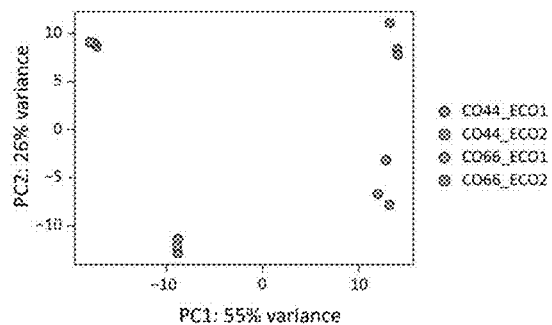
[FIGS. 7A-7B]
A
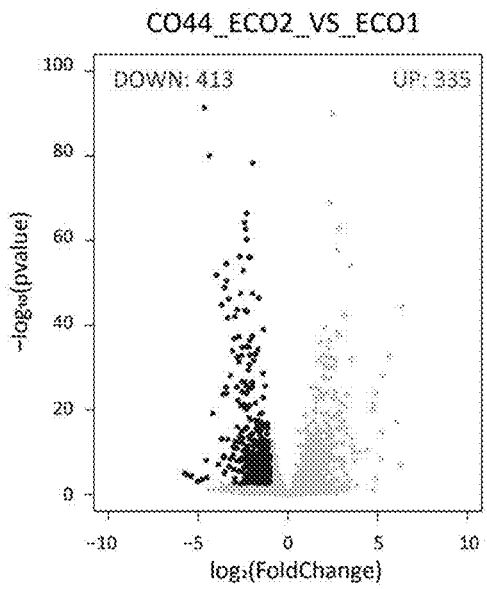
B
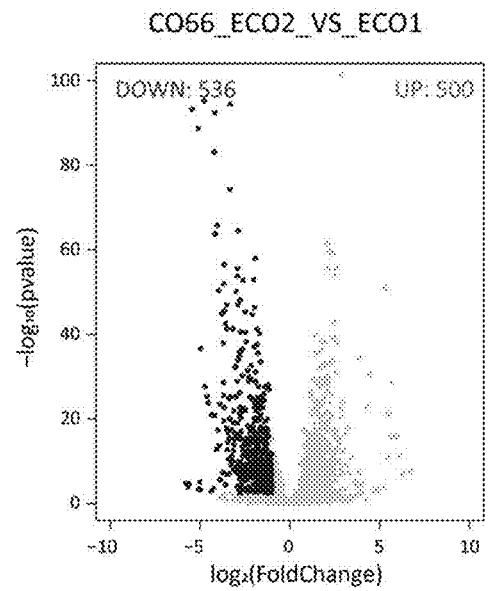

[FIGS. 8A-8B]
A
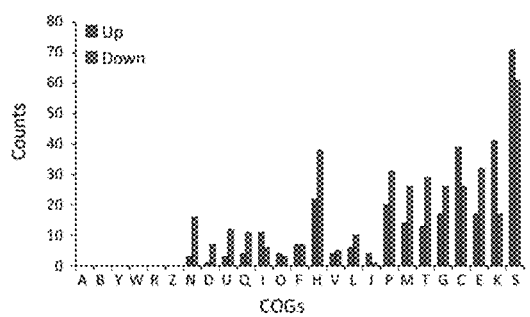
B
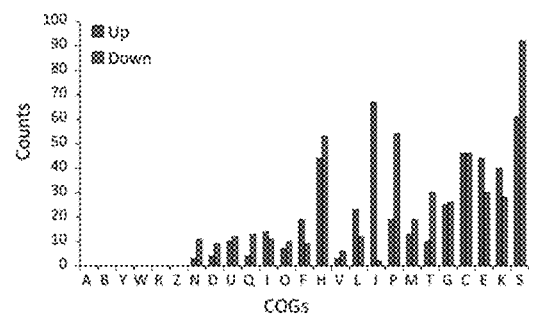

[FIGS. 9A-9B]
A
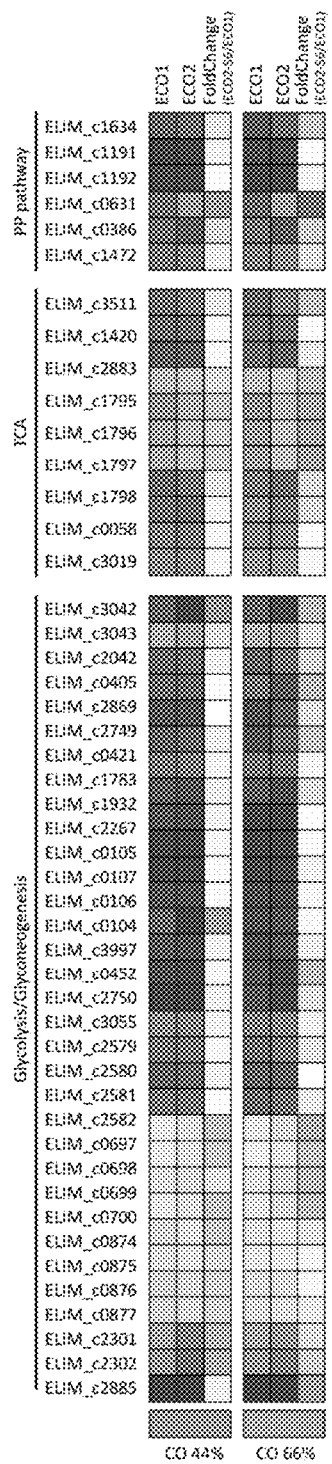
B
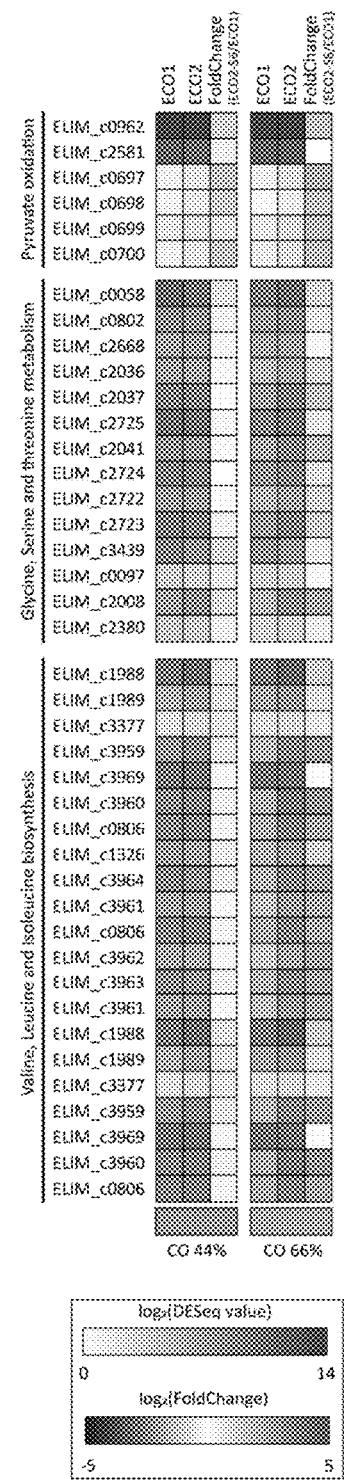

[FIG. 10]
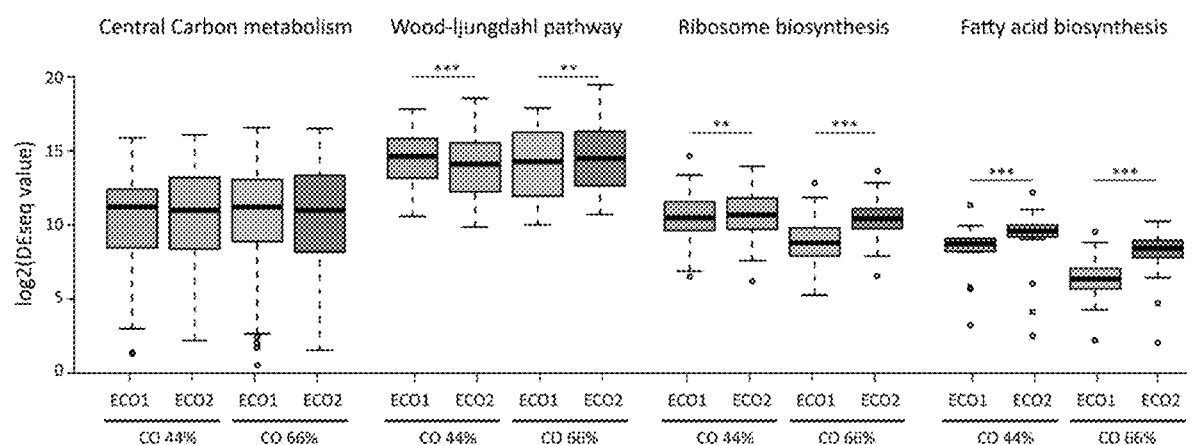

[FIG. 11]
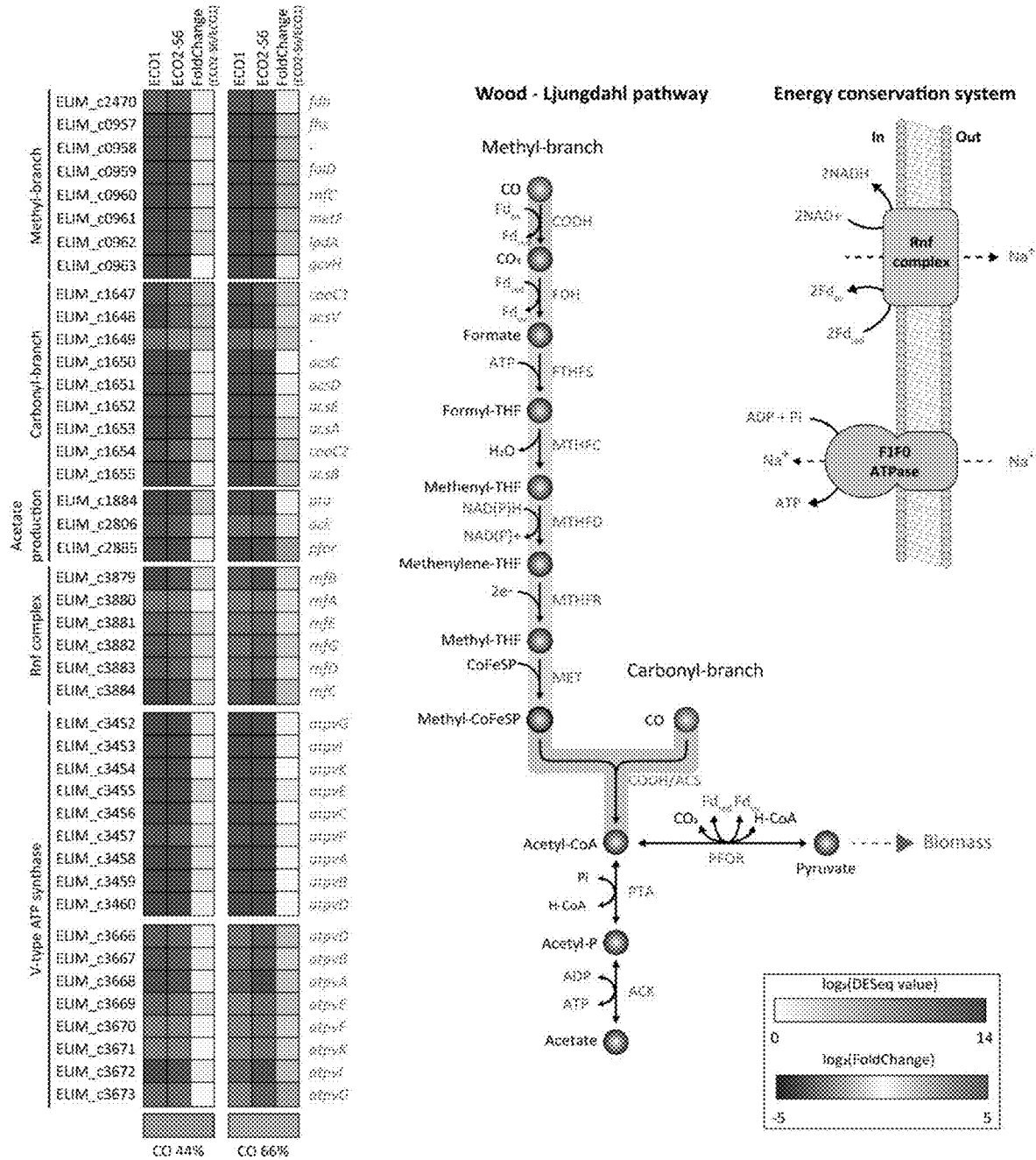

[FIGS. 12A-12D]
A
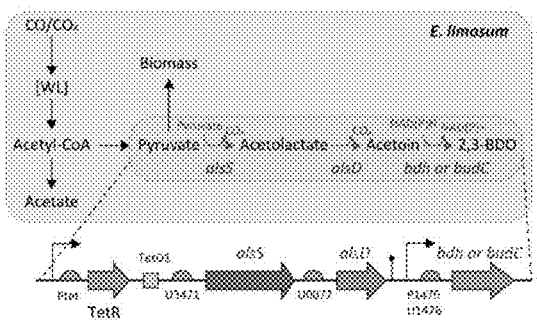
B
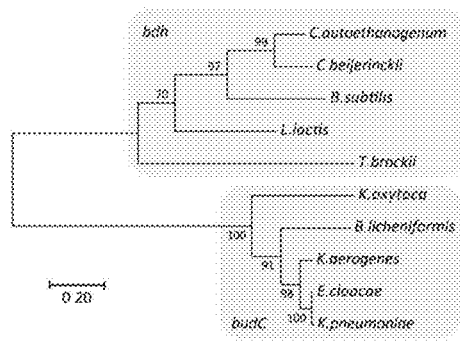
C
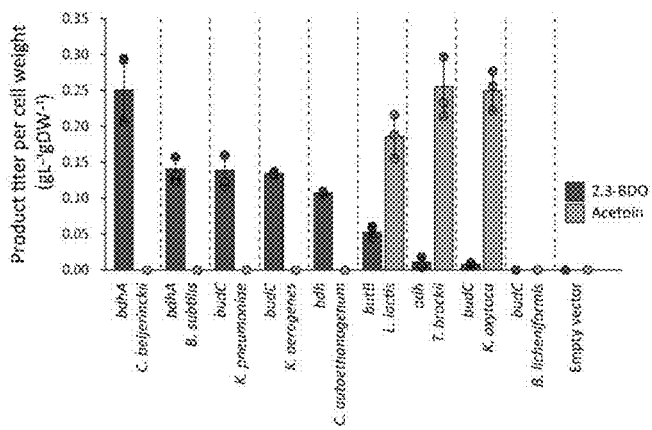
D
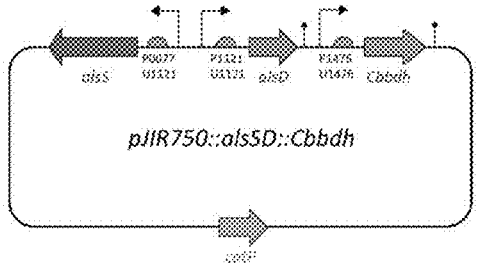

[FIGS. 13A-13D]
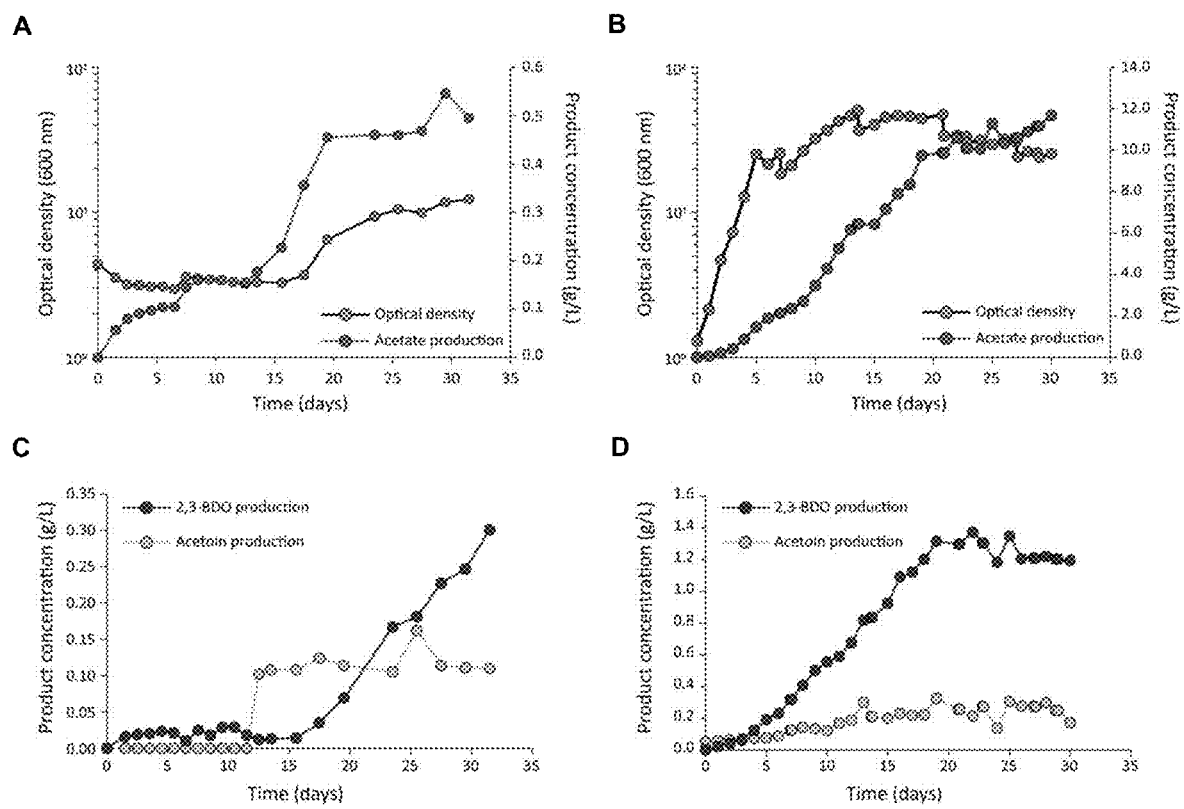

MICROORGANISM WITH INCREASED CARBON MONOXIDE AVAILABILITY AND 2,3-BDO PRODUCTION USING THE SAME

BACKGROUND OF THE INVENTION

This application claims priority to Korean Patent Application No. 10-2022-0102140, entitled "MICROORGANISM WITH INCREASED CARBON MONOXIDE AVAILABILITY AND 2,3-BDO PRODUCTION USING THE SAME," filed on Aug. 16, 2022, the entirety of which is incorporated herein by reference.

INCORPORATION OF SEQUENCE LISTING

The sequence listing that is contained in the file named "HANOP0044US.xml", which is 50,817 bytes (as measured in Microsoft Windows®) and created on Jul. 25, 2024, is filed herewith by electronic submission, and is incorporated by reference herein.

TECHNICAL FIELD

The present invention relates to a microorganism with increased carbon monoxide availability and use thereof.

BACKGROUND ART

The recently emerging carbon resource conversion technology is a technology that utilizes carbon monoxide, carbon dioxide, methane, natural gas, etc. generated from fossil fuels as raw materials to turn it into resources, and is attracting attention as a new industry creation item because it is effective in greenhouse gas reduction and energy self-sufficiency, etc.

Waste gas (synthesis gas) is a mixture gas composed of carbon monoxide (CO), carbon dioxide ($CO_2$), and hydrogen ($H_2$) obtained through the gasification process of various carbon-based raw materials such as waste, coal, coke, low-grade hydrocarbon gas, naphtha, heavy oil, etc., which is referred to as syngas or waste gas. The group of microorganisms that produce acetic acid by anaerobic metabolism using synthetic gas or sugar as a carbon and energy source is called "acetogen". Acetogen uses the waste gas as a carbon and energy source to produce organic acids such as butyric acid, and bioalcohols such as ethanol and butanol, in addition to acetic acid, which is the major product (HL Drake et al., Annals of the New York Academy of Sciences, 1125:100, 2008).

To date, more than 100 kinds of acetogen bacteria are known, but only a few strains produce 4-carbon organic substances such as butyric acid by consuming waste gas. In addition, it is very rare for the metabolic engineering for the increase of metabolite productivity in acetogen to be successfully performed and commercialized because it is very difficult to establish a genetic engineering system suitable for acetogen, a completely Gram-positive anaerobic strain, and the self-growth of acetogen at high CO concentrations is extremely limited.

Under such circumstances, the present inventors have evolved microorganisms by applying stress to the CO concentration in order to develop microorganisms whose growth level does not fall even under high CO concentration conditions, and as a result, they have confirmed that microorganisms having improved CO availability by adapting to a high CO concentration environment contain a mutation in the ACS protein, and identified that this protein variant was involved in improving the CO availability of the microorganisms, thereby completing the present invention.

DISCLOSURE

Technical Problem

It is one object of the present invention to provide an acetyl-CoA synthase variant, in which histidine at position 636 from the N-terminus of acetyl-CoA synthase derived from a microorganism of the genus *Eubacterium limosum* is substituted with another amino acid.

It is another object of the present invention to provide a microorganism including the variant.

It is still another object of the present invention to provide a method for preparing a compound, including: culturing the microorganism.

It is yet another object of the present invention to provide a method for removing carbon monoxide gas, including: culturing the microorganism under gas conditions containing carbon monoxide (CO).

Technical Solution

The present invention will be described in detail as follows. Meanwhile, each description and embodiment disclosed herein can be applied to other descriptions and embodiments, respectively. That is, all combinations of various elements disclosed herein fall within the scope of the present invention. Further, the scope of the present application is not limited by the specific description described below.

Additionally, a number of papers and patent documents have been cited throughout the present specification. The content of the cited papers and patent documents is incorporated herein by reference in its entirety, and the level of the technical field to which the present invention belongs and the contents of the present invention will be described more clearly.

Additionally, those of ordinary skill in the art may be able to recognize or confirm, using only conventional experimentation, many equivalents to the particular aspects of the invention described herein. Furthermore, it is also intended that these equivalents be included in the present invention.

One aspect of the present invention provides an acetyl-CoA synthase variant, in which histidine at position 636 from the N-terminus of acetyl-CoA synthase derived from a microorganism of the genus *Eubacterium* is substituted with another amino acid.

In one embodiment, the variant provided by the present invention is a variant in which histidine at position 636 from the N-terminus is substituted with another amino acid based on the amino acid sequence of SEQ ID NO: 1 in any protein having acetyl-CoA activity. In particular, SEQ ID NO: 1 is used as a reference sequence for indicating a mutation position.

In any one of the above-described embodiments, the acetyl COA synthase, which is a protein targeted for mutation for the variant provided in the present invention, may also be referred to as "CODH/ACS complex subunit beta", and can form carbon monoxide dehydrogenase (CODH)/acetyl-CoA synthase (ACS) complexes.

In any one of the above-described embodiments, the acetyl-CoA synthase, which is a protein targeted for mutation for the variant provided in the present invention, may be an acetyl-CoA synthase derived from *Eubacterium limosum*.

In any one of the above-described embodiments, the acetyl-CoA synthase, which is a protein targeted for mutation for the variant provided in the present invention, may include SEQ ID NO: 1, or may consist essentially or consist of the same. However, it does not exclude a mutation that may occur by a meaningless sequence addition upstream or downstream of the amino acid sequence of SEQ ID NO: 1 or that may occur naturally, or a silent mutation thereof, and it is apparent to those skilled in the art that any protein having the same or corresponding activity to the protein composed of the amino acid sequence of SEQ ID NO: 1 may fall within the acetyl-CoA synthase of the present invention.

In a specific example, the acetyl-CoA synthase of the present may be a protein consisting of the amino acid sequence of SEQ ID NO: 1, or an amino acid sequence having a homology or identity to the amino acid sequence of SEQ ID NO: 1 of 80%, 82%, 86%, 90%, 95%, 97%, 98% or 99% or higher. Additionally, it is apparent that any protein having an amino acid sequence with deletion, modification, substitution, or addition in part of the sequence belongs to the scope of the protein targeted for mutation of the present invention as long as the protein has an amino acid sequence with any of the above homologies and identities, and exhibits an effect corresponding to the above protein.

That is, in the present invention, although it is described as "a protein or polypeptide having an amino acid sequence of a particular SEQ ID NO" or "a protein or polypeptide consisting of an amino acid sequence of a particular SEQ ID NO", it is apparent that any protein which has deletion, modification, substitution, or addition in part of the amino acid sequence may also be used in the present invention, as long as the protein has the same or corresponding activity to the polypeptide composed of the amino acid sequence of the corresponding SEQ ID NO. For example, it is apparent that the "polypeptide composed of the amino acid sequence of SEQ ID NO: 1" may fall within the "polypeptide composed of the amino acid sequence of SEQ ID NO: 1" as long as the polypeptide has the same or corresponding activity.

As used herein, the term "variant" refers to a protein having one or more amino acids different from the recited sequence by conservative substitutions and/or modifications such that the functions and properties of the protein are retained. The variants are different from the sequences identified by substitution, deletion or addition of several amino acids. Such variants may generally be identified by modifying one or more of the above amino acid sequences of the protein and evaluating the properties of the modified protein. That is, the ability of the variants may be enhanced, unchanged or reduced relative to a native protein. Additionally, some variants may include those in which one or more regions, such as an N-terminal leader sequence or transmembrane domain, have been removed. Other variants may include those in which a region has been removed from the N- and/or C-terminus of a mature protein. The term "variant" may be used interchangeably with terms such as modification, modified protein, modified polypeptide, mutant, mutein, divergent, variant, etc., as long as the terms are used to indicate variation, but the terms are not limited thereto.

As used herein, the term "conservative substitution" refers to substitution of an amino acid with another amino acid having similar structural and/or chemical properties. The variant may have, for example, one or more conservative substitutions while still retaining one or more biological activities. Such amino acid substitution may generally occur based on similarity of polarity, charge, solubility, hydrophobicity, hydrophilicity, and/or amphipathic nature of a residue. For example, among the amino acids having an electrically charged side chain, positively charged (basic) amino acids include arginine, lysine, and histidine; negatively charged (acidic) amino acids include glutamic acid and aspartic acid. Further, among the amino acids having an uncharged side chain, nonpolar amino acids include glycine, alanine, valine, leucine, isoleucine, methionine, phenylalanine, tryptophan, and proline; polar or hydrophilic amino acids include serine, threonine, cysteine, tyrosine, asparagine, and glutamine; and aromatic amino acids include phenylalanine, tryptophan and tyrosine.

Additionally, the variant may also include deletion or addition of amino acids that have minimal influence on the properties and secondary structure of a polypeptide. For example, the polypeptide may be conjugated with a signal (or leader) sequence at the N-terminus involved in the transfer of proteins co-translationally or post-translationally. Further, the polypeptide may also be conjugated with another sequence or linker to identify, purify, or synthesize the polypeptide.

The "substitution with another amino acid" is not limited as long as it is substituted with an amino acid other than the amino acid before substitution. For example, the substitution of histidine at position 636 with another amino acid means substitution with an amino acid residue other than histidine. Meanwhile, in the present invention, when it is expressed that "a specific amino acid has been substituted", it is apparent that the amino acid is substituted with an amino acid different from the amino acid before substitution, even if it is not specifically stated that the amino acid has been substituted with a different amino acid.

In one embodiment, the protein variant may be one in which the amino acid at position 636 of the amino acid sequence of SEQ ID NO: 1 is substituted with lysine or arginine, specifically, the amino acid at position 636 may be substituted with arginine, but is not limited thereto.

In any one of the above-described embodiments, the protein variant of the present invention has may include a polypeptide having a homology or identity of 80%, 90%, 95%, 96%, 97%, 98%, 99% or higher or 100% to the amino acid sequence of SEQ ID NO: 3. Additionally, it is apparent that any protein having an amino acid sequence, in which part of the amino acid sequence is deleted, modified, substituted, or added, may fall within the scope of the present invention, as long as the amino acid sequence has such homology or identity and shows an efficacy corresponding to that of the protein.

In any one of the above-described embodiments, the amino acid at position 475 from the N-terminus of the protein variant may be aspartic acid (D).

In any one of the above-described embodiments, the amino acid at position 476 from the N-terminus of the protein variant may be aspartic acid (D).

In any one of the above-described embodiments, the amino acids at positions 475 and 476 from the N-terminus of the protein variant may be aspartic acid (D).

In the variant of the present invention, the amino acid at position 636 may be substituted with another amino acid to enhance the interaction with amino acids at positions 475 and/or 476.

As used herein, the term "homology" or "identity" refers to a degree of relatedness between two given amino acid sequences or nucleotide sequences, and may be expressed as a percentage. The terms homology and identity may often be used interchangeably with each other.

The sequence homology or identity of conserved polynucleotides or polypeptides may be determined by standard alignment algorithms and can be used with a default gap penalty established by the program being used. Substantially, homologous or identical sequences may hybridize under moderately or highly stringent conditions such that the full length of the sequence or at least about 50%, 60%, 70%, 80%, or 90% or more of the full length may hybridize. Polynucleotides that contain degenerate codons instead of codons in hybridizing polynucleotides are also considered.

Whether any two polynucleotide or polypeptide sequences have a homology, similarity, or identity may be, for example, determined by a known computer algorithm such as the "FASTA" program (Pearson et al., (1988) Proc. Natl. Acad. Sci. USA 85:2444) using default parameters. Alternatively, it may be determined by the Needleman-Wunsch algorithm (Needleman and Wunsch, 1970, J. Mol. Biol. 48:443-453), which is performed using the Needleman program of the EMBOSS package (EMBOSS: The European Molecular Biology Open Software Suite, Rice et al., 2000, Trends Genet. 16:276-277) (preferably, version 5.0.0 or later) (GCG program package (Devereux, J., et al., Nucleic Acids Research 12:387 (1984)), BLASTP, BLASTN, FASTA (Atschul, S. F. et al., J MOLEC BIOL 215:403 (1990); Guide to Huge Computers, Martin J. Bishop, ed., Academic Press, San Diego, 1994, and CARILLO et al. (1988) SIAM J Applied Math 48:1073). For example, the homology, similarity, or identity may be determined using BLAST or ClustalW of the National Center for Biotechnology Information (NCBI).

The homology, similarity, or identity of polynucleotides or polypeptides may be, for example, determined by comparing sequence information using, for example, the GAP computer program, such as Needleman et al. (1970), J Mol Biol. 48:443 as disclosed in Smith and Waterman, Adv. Appl. Math (1981) 2:482. In summary, the GAP program defines the homology, similarity, or identity as the value obtained by dividing the number of similarly aligned symbols (i.e., nucleotides or amino acids) by the total number of the symbols in the shorter of the two sequences. Default parameters for the GAP program may include (1) a unary comparison matrix (containing a value of 1 for identities and 0 for non-identities) and the weighted comparison matrix of Gribskov et al. (1986), Nucl. Acids Res. 14:6745, as disclosed in Schwartz and Dayhoff, eds., Atlas of Protein Sequence and Structure, National Biomedical Research Foundation, pp. 353-358 (1979) (or EDNAFULL substitution matrix (EMBOSS version of NCBI NUC4.4)); (2) a penalty of 3.0 for each gap and an additional 0.10 penalty for each symbol in each gap (or a gap opening penalty of 10 and a gap extension penalty of 0.5); and (3) no penalty for end gaps.

Further, whether any two polynucleotide or polypeptide sequences have a homology, similarity or identity with each other may be identified by comparing the sequences in a Southern hybridization experiment under stringent conditions as defined, and appropriate hybridization conditions defined are within the skill of the art, and may be determined by a method well known to those skilled in the art (e.g., J. Sambrook et al., *Molecular Cloning, A Laboratory Manual*, 2nd Edition, Cold Spring Harbor Laboratory press, Cold Spring Harbor, New York, 1989; F. M. Ausubel et al., *Current Protocols in Molecular Biology*, John Wiley & Sons, Inc., New York).

Another aspect of the present invention provides a polynucleotide encoding the protein variant.

As used herein, the term "polynucleotide", which is a polymer of nucleotides composed of nucleotide monomers connected in a lengthy chain by a covalently bond, is a DNA or RNA strand having at least a certain length. More specifically, it may refer to a polynucleotide fragment encoding the protein variant.

In the present invention, the gene encoding the amino acid sequence of SEQ ID NO: 1 having acetyl-CoA synthase activity may be referred to as "acsB gene". For example, the gene encoding the acetyl-CoA synthase may be a sequence including the nucleotide sequence of SEQ ID NO: 2, but is not limited thereto.

The polynucleotide encoding the protein variant of the present invention may undergo various modifications in the coding region within the scope that does not change the amino acid sequence of the polypeptide, due to codon degeneracy or in consideration of the codons preferred in an organism in which the polypeptide is to be expressed. Specifically, any polynucleotide sequence encoding the protein variant, in which the amino acid at position 636 in the amino acid sequence of SEQ ID NO: 1 is substituted with another amino acid, may be included without limitation.

Further, the polynucleotide encoding the protein variant may include a probe that may be prepared from a known gene sequence, for example, any sequence encoding the protein variant, in which the amino acid at position 636 in the amino acid sequence of SEQ ID NO: 1 is substituted with another amino, by hybridizing with a sequence complementary to all or part of the polynucleotide sequence under stringent conditions without limitation.

The "stringent conditions" refers to conditions under which specific hybridization between polynucleotides is allowed. Such conditions are specifically described in the literature (J. Sambrook et al., supra). Hybridization requires that two polynucleotides contain complementary sequences, although mismatches between bases are possible depending on the stringency of the hybridization. The term "complementary" is used to describe the relationship between nucleotide bases that can hybridize with each other. For example, with respect to DNA, adenine is complementary to thymine, and cytosine is complementary to guanine. Therefore, the present invention may include isolated polynucleotide fragments complementary to the entire sequence as well as polynucleotide sequences substantially similar thereto. The appropriate stringency for hybridizing the polynucleotides depends on the length of the polynucleotides and the degree of complementation, and these variables are well known in the art.

The polynucleotide encoding the protein variant of the present invention may be a polynucleotide in which adenine (A) at position 1907 in the nucleotide sequence of SEQ ID NO: 2 is substituted with another base, specifically, adenine (A) at position 1907 in the nucleotide sequence of SEQ ID NO: 2 may be substituted with guanine (G), and more specifically, the polynucleotide may include the nucleotide sequence of SEQ ID NO: 4, but is not limited thereto.

Still another aspect of the present invention provides a vector containing a polynucleotide encoding the protein variant.

As used herein, the term "vector" refers to a DNA construct containing the nucleotide sequence of a polynucleotide encoding the target protein operably linked to a suitable expression regulatory sequence so as to be able to express the target protein in a suitable host cell. The expression regulatory sequence may include a promoter capable of initiating transcription, any operator sequence for regulating the transcription, a sequence encoding a suitable mRNA ribosome binding site, and a sequence for regulating termination of transcription and translation. Once transformed into a suitable host cell, the vector may replicate or function independently from the host genome, or may integrate into genome thereof.

The vector used in the present invention is not particularly limited, and any vector known in the art may be used. Examples of the vector typically used may include natural or recombinant plasmids, cosmids, viruses, and bacteriophages. Examples of the vector that can be used in the present invention include pJIR750ai, but the vector is not particularly limited thereto.

In one example, a polynucleotide encoding a target protein in the chromosome may be replaced with a modified polynucleotide through a vector for intracellular chromosomal insertion. The insertion of the polynucleotide into the chromosome may be performed by any method known in the art, for example, by homologous recombination, but is not limited thereto. The vector may further include a selection marker to confirm the insertion into the chromosome. The selection marker is for selecting the cells transformed with the vector, that is, for confirming whether the target nucleic acid molecule has been inserted, and markers that provide selectable phenotypes, such as drug resistance, auxotrophy, resistance to cell toxic agents, or expression of surface proteins, may be used. Only cells expressing the selection marker are able to survive or to show different phenotypes under the environment treated with the selective agent, and thus the transformed cells may be selected.

Yet another aspect of the present invention provides a microorganism including the protein variant.

In the present invention, the microorganism may be acetogen. The "acetogen" refers to a group of microorganisms that produce acetic acid through anaerobic metabolism using syngas or sugar as a carbon and energy source. Acetogen may be a microorganism capable of carrying out the Wood-Ljungdahl pathway, or may be a microorganism capable of converting CO, $CO_2$, and/or $H_2$ to acetate. The microorganism includes all genetically modified microorganisms by natural or artificial means, and may be a microorganism in which a particular mechanism is weakened or enhanced due to insertion of a foreign gene, or enhancement or weakening of the activity of an endogenous gene. In addition, the microorganism may be a microorganism in which a genetic mutation is introduced or activity is enhanced according to the purpose.

In one example, the microorganism may be a microorganism of the genus *Eubacterium*. In one example, the microorganism may be *Acetoanaerobiumnotera* (ATCC 35199), *Acetonemalongum* (DSM 6540), *Acetobacterium carbinolicum* (DSM 2925), *Acetobacterium malicum* (DSM 4132), *Acetobacterium* sp. No. 446 (Morinaga et al., 1990, *J. Biotechnol.*, Vol. 14, pp. 187-194), *Acetobacterium wieringae* (DSM 1911), *Acetobacterium woodii* (DSM 1030), *Alkalibaculumbacchi* (DSM 22112), *Archaeoglobusfulgidus* (DSM 4304), *Blautiaproducta* (DSM 2950, previously known as *Ruminococcus productus*, previously known as *Peptostreptococcus productus*), *Butyribacterium methylotrophicum* (DSM 3468), *Clostridium aceticum* (DSM 1496), *Clostridium autoethanogenum* (DSM 10061, DSM 19630 and DSM 23693), *Clostridium carboxidivorans* (DSM 15243), *Clostridium coskatii* (ATCC No. PTA-10522), *Clostridium drakei* (ATCC BA-623), *Clostridium formicoaceticum* (DSM 92), *Clostridium glycolicum* (DSM 1288), *Clostridium ljungdahlii* (DSM 13528), *Clostridium ljungdahlii* C-01 (ATCC 55988), *Clostridium ljungdahlii* ERI-2 (ATCC 55380), *Clostridium ljungdahlii* O-52 (ATCC 55989), *Clostridium mayombei* (DSM 6539), *Clostridium methoxybenzovorans* (DSM 12182), *Clostridium ragsdalei* (DSM 15248), *Clostridium scatologenes* (DSM 757), *Clostridium*) sp. ATCC 29797 (Schmidt et al., 1986, *Chem. Eng. Commun.*, Vol. 45, pp. 61-73), *Desulfotomaculum kuznetsovii* (DSM 6115), *Desulfotomaculum thermobezoicum* subsp. *thermosyntrophicum* (DSM 14055), *Eubacteriumlimosum*, *Methanosarcina acetivorans* C2A (DSM 2834), *Moorella*) sp. HUC22-1 (Sakai et al., 2004, *Biotechnol. Lett.*, Vol. 29, pp. 1607-1612), *Moorella thermoacetica* (DSM 521, previously known as *Clostridium thermoaceticum*), *Moorella thermoautotrophica* (DSM 1974), *Oxobacterpfennigii* (DSM 322), *Sporomusa aerivorans* (DSM 13326), *Sporomusa ovata* (DSM 2662), *Sporomusa silvacetica* (DSM 10669), *Sporomusa sphaeroides* (DSM 2875), *Sporomusa termitida* (DSM 4440), *Thermoanaerobacter kivui*, etc. Specifically, the microorganism may be selected from *Acetobacterium woodii*, *Thermoanaerobacter kivui*, and *Eubacterium limosum*, more specifically *Eubacterium limosum*.

The protein variant of the present invention may be those capable of improving CO availability of microorganisms containing the same, and the microorganisms may be those having improved CO availability compared to microorganisms that do not include the protein variant of the present invention.

As used herein, the "improvement of CO availability" may include the meanings of "increased carbon monoxide fixing ability", "increased carbon monoxide tolerance", etc., and shows a higher growth rate than native microorganisms in the presence of carbon monoxide in the culture environment, or may appear as a phenotype such as mass production of metabolites.

In any one of the above-described embodiments, the microorganism of the present invention may further include any one or more mutations shown in Table 1 below.

TABLE 1

| Locus tag | Gene | Mutation (Type) | AA change | Description |
|---|---|---|---|---|
| ELIM_c1653 | acsA | C290A (SNV) | Ala97Glu | CODH catalytic subunit |
| ELIM_c1031 | — | —356T (insertion) | Asn119Lys | Integrase family protein |
| ELIM_c1038 | — | G133A (SNV) | Glu48Lys | Putative ATPase, transposase-like protein |
| ELIM_c1073 | dam | T408G (SNV) | Tyr136X133 | N6 adenine-specific DNA methylase D12 class |
| ELIM_c1654 | cooC2 | —216A (insertion) | Ala72fsX92 | CODH nickel insertion accessory protein |
| ELIM_c1655 | acsB | A1907G (SNV) | His636Arg | CODH/ACS complex subunit beta |
| ELIM_c1653 | acsA | C275T (SNV) | Ala92Val | CODH catalytic subunit |
| ELIM_c2589 | — | G148A (SNV) | Asp50Asn | hypothetical protein |
| ELIM_c2589 | — | C195T (SNV) | | hypothetical protein |

TABLE 1-continued

| Locus tag | Gene | Mutation (Type) | AA change | Description |
|---|---|---|---|---|
| ELIM_c0006 | — | G1265T (SNV) | Ala$^{422}$Glu | Gp11 |
| ELIM_c2214 | — | —413G (insertion) | Arg$^{138}$Arg | Hypothetical protein |
| ELIM_c2227 | — | G82T (SNV) | Ala$^{28}$Ser | Terminase |

In any one of the above-described embodiments, the microorganism of the present invention may further include any one or more mutations shown in Table 2 below.

TABLE 2

| Samples | Locus tag | Position | Type | Reference | Allele | AA change |
|---|---|---|---|---|---|---|
| ECO_acs | ELIM_c1653 | 1,832,907 | SNV | C | T | Ala$^{92}$Val |
| A, 2, 3, 4 | | 1,832,922 | SNV | C | A | Ala$^{97}$Glu |
| 1, 2, 3, 4 | ELIM_c1031 | 1,126,411 | Insertion | — | T | Asn$^{119}$LysfsX132 |
| 1, 2, 3, 4 | Intergenic | 1,970,647 | SNV | G | A | — |
| 1, 2, 3 | ELIM_c1654 | 1,834,784 | Insertion | — | A | Ala$^{72}$AlafsX92 |
| 1, 2, 3 | ELIM_c3581 | 3,896,831 | SNV | C | A | Asp$^{66}$Tyr |
| 1, 2, 3 | Intergenic | 1,972,135 | SNV | T | C | — |
| 1, 2, 4 | ELIM_c1038 | 1,130,590 | SNV | G | A | Glu$^{48}$Lys |
| 1, 2, 4 | ELIM_c1073 | 1,159,055 | SNV | T | G | Tyr$^{136}$X |
| 1, 4 | ELIM_c0527 | 588,552 | Deletion | C | — | Gly$^{279}$ValfsX282 |
| 1 | ELIM_c0236 | 256,802 | SNV | G | T | Ser$^{348}$X |
| 1 | ELIM_c0337 | 370,333 | SNV | C | G | Glu$^{315}$Gln |
| 1 | ELIM_c0437 | 483,053 | SNV | G | A | Ala$^{185}$Val |
| 1 | ELIM c0530 | 592,464 | SNV | G | A | Ile$^{774}$Ile |
| 1 | ELIM_c0659 | 726,708 | SNV | G | C | Pro$^{74}$Arg |
| | | 726,714 | SNV | T | C | Asp$^{72}$Gly |
| 1 | ELIM_c0672 | 739,966 | SNV | C | A | Ala$^{88}$Ser |
| 1 | ELIM_c0750 | 832,772 | SNV | G | C | Ala$^{326}$Ala |
| 1 | ELIM_c0854 | 938,560 | SNV | A | G | Lys$^{490}$Arg |
| 1 | ELIM_c0866 | 952,049 | SNV | G | A | Val$^{789}$Val |
| 1 | ELIM_c1063 | 1,148,482 | SNV | G | T | Gly$^{741}$Trp |
| 1 | ELIM_c1325 | 1,436,020 | SNV | A | G | Ile$^{865}$Thr |
| 1 | ELIM_c2814 | 3,101,419 | SNV | C | A | Ala$^{63}$Ala |
| 1 | ELIM_c2882 | 3,162,881 | SNV | G | A | Gly$^{38}$Arg |
| 1 | ELIM_c2942 | 3,240,199 | SNV | C | A | Arg$^{143}$Arg |
| 1 | ELIM_c3150 | 3,443,977 | SNV | T | C | Asp$^{310}$Gly |
| 1 | ELIM_c3386 | 3,699,117 | SNV | T | A | Leu$^{144}$X |
| 1 | ELIM_c3427 | 3,747,388 | SNV | G | T | Asp$^{56}$Tyr |
| 1 | ELIM_c3691 | 3,999,914 | SNV | C | A | Met$^{194}$Ile |
| 1 | Intergenic | 3,309,964 | SNV | A | T | — |
| 2 | ELIM_c2071 | 2,255,729 | SNV | C | A | Gly$^{14}$Val |
| 2 | ELIM_c2621 | 2,852,312 | SNV | G | C | Leu$^{152}$Leu |
| 2 | ELIM_c3002 | 3,306,141 | SNV | C | T | Ser$^{47}$Ser |
| 2 | Intergenic | 3,183,238 | SNV | G | C | — |
| 2 | Intergenic | 3,305,753 | SNV | G | A | — |
| 3 | ELIM_c0293 | 322,696 | SNV | G | T | Ile$^{170}$Ile |
| 4 | ELIM_c0006 | 5,401 | SNV | G | T | His$^{99}$Asn |
| 4 | ELIM c1330 | 1,446,536 | SNV | G | A | Val$^{392}$Val |
| 4 | Intergenic | 1,946,081 | SNV | G | C | — |

In any one of the above-described embodiments, the microorganism of the present invention may further include additional modifications of the Wood-Ljungdal pathway.

In any one of the above-described embodiments, the microorganism of the present invention may further include genes necessary for acetoin synthesis. The microorganism may further include, for example, an alsS gene and an alsD gene. The alsS gene encodes an enzyme that converts pyruvic acid to acetolactate, and the alsD gene encodes an enzyme that converts acetolactate to acetoin. In one example, the microorganism may include an alsS gene derived from *Bacillus subtilis* and an alsD gene derived from *Aeromonas hydrophila*.

In any one of the above-described embodiments, the microorganism of the present invention may further include a gene encoding an enzyme that converts acetoin into alcohol. For example, the alcohol may be ethanol, 2,3-butanediol (2,3-BDO) or isopropyl alcohol. In one example, the alcohol may be 2,3-BDO.

In any one of the above-described embodiments, the microorganism of the present invention may further include a gene necessary for 2,3-BDO synthesis. For example, the microorganism may further include a bdh or budC gene. The bdh gene and the budC gene each independently encode 2,3-butanediol dehydrogenase, and this enzyme can convert acetoin into 2,3-BDO.

In any one of the above-described embodiments, the microorganism of the present invention may include an alsS gene; an alsD gene; and a bdh or budC gene.

Even another aspect of the present invention provides a method for preparing a compound, including: culturing the microorganism of the present invention.

In one embodiment, the microorganism may be acetogen, which is the same as described above.

In any one of the above-described embodiments, the compound may be selected from acetoin and alcohol. In any one of the above-described embodiments, the compound may be selected from acetoin and 2,3-BDO, and in one example, the compound may be 2,3-BDO. The compound is the same as described above.

As used herein, the term "cultivation" means that the microorganism is grown under appropriately controlled environmental conditions. The cultivation process of the present invention may be performed in a suitable culture medium and culture conditions known in the art. Such a cultivation process may be easily adjusted for use by those skilled in the art according to the strain to be selected. Specifically, the cultivation may be a batch culture, a continuous culture, and a fed-batch culture, but is not limited thereto. The cultivation includes not only a process of growing the acetogenic microorganism in the culture medium, but also a process of assimilating, catabolizing, or converting a substrate provided in the culture medium, although the cells do not grow.

As used herein, the term "medium" refers to a mixture of materials which contains nutrient materials required for the cultivation of the microorganism as a main ingredient, and it supplies nutrient materials and growth factors, along with water that is essential for survival and growth. Specifically, the medium and other culture conditions used for culturing the microorganism of the present invention may be any medium used for conventional cultivation of acetogenic microorganisms without limitation. Additionally, the microorganism of the present invention may be cultured under aerobic conditions in a conventional medium containing an appropriate carbon source, nitrogen source, phosphorus source, inorganic compound, amino acid, and/or vitamin, while adjusting temperature, pH, etc. In one embodiment, in the present invention, the carbon source may be syngas, for example, CO or $CO_2$, and specifically CO, but is not limited thereto.

In addition, during the microbial cultivation process of the present invention, syngas containing gas such as $H_2$ in addition to CO and $CO_2$ may be supplied. The gas may further include $N_2$, but is not limited thereto. It may be a mixed gas composed of carbon monoxide (CO), carbon dioxide ($CO_2$), and hydrogen ($H_2$) obtained through the gasification process of various carbon-based raw materials such as waste, coal, coke, low-grade hydrocarbon gas, naphtha, heavy oil, etc., but is not limited thereto.

Further another aspect of the present invention provides a method for removing carbon monoxide gas, including: culturing a microorganism including the variant of the present invention under gas conditions containing carbon monoxide (CO).

The method may include the step of converting CO into another substance by the microorganism.

Advantageous Effects

The variant of the present invention has improved CO availability, and the microorganism including the same can survive even under a high CO concentration, and since the microorganism can produce useful products using CO as a substrate, it can be effectively used not only for the production of industrially valuable compounds, but also for the removal of waste gases.

BRIEF DESCRIPTION OF DRAWINGS

FIGS. 1A-1E show the growth of E. limosum wild type (WT), ECO1, or ECO2 strains under various CO syngas conditions. FIG. 1A is the growth profiling of E. limosum WT or ECO1 strain under the CO 60% syngas condition, FIG. 1B is a comparison of the growth rate according to the CO concentrations, FIG. 1C is the adaptive laboratory evolution of E. limosum ECO1 strain under the CO 66% syngas condition, FIG. 1D is the growth profiling of E. limosum WT, ECO, and ECO2-P strains under CO 66% syngas conditions, and FIG. 1E is the relative growth rate of E. limosum WT, ECO1, and ECO2-P according to the CO concentrations. Error bars represent standard deviations (P; population).

FIGS. 2A-2B are a comparison of the isolation and CO gas consumption rates of ECO2 single strains. FIG. 2A is the growth rate of ECO2 single colony under the CO 66% syngas condition, and FIG. 2B is the result of confirming the optical density or CO gas consumption of E. limosum ECO1 and ECO2-S6. Error bars represent standard deviations.

FIGS. 3A-3D are a hypothesis for the $H_{636}R$ mutation in the ECO2 CODH/ACS complex. FIG. 3A is a structural change of the CODH/ACS complex, FIG. 3B is a hypothesis for the conformational change of the ECO2 CODH/ACS complex, FIG. 3C is a vector construct for expressing CODH/ACS complex in E. limosum WT, and FIG. 3D is the growth profiling of several CODH/ACS-expressing E. limosum in mixed nutrient culture (66% CO+5 g/L glucose). Error bars represent standard deviations.

FIGS. 4A-4B are a comparison of the biomass increase rate and the CO gas absorption rate of the ECO1 strain and the ECO2-S6 strain. FIG. 4A is a comparison of microbial biomass increase rate, and FIG. 4B is a comparison of CO gas absorption rate. Error bars represent standard deviations.

FIGS. 5A-5C predict the structure of the ACS protein of E. limosum microorganisms using the AlphaFold2 structure prediction program. FIG. 5A is a comparison of the structure of the ACS protein of M. thermoacetica microorganism and the ACS protein of E. limosum, FIG. 5B is a comparison of the E. limosum WT and ECO2 strains for the amino acid residue at position 636 in which the mutation occurred, and FIG. 5C is a comparison of the structure of the ACS protein having H636R mutation with the wild type and variant.

FIGS. 6A-6B are a comparison of Hierarchical clustering (H-clustering) distance analysis and Principal component analysis (PCA) between transcript data under a CO 44% condition and a CO 66% syngas condition of E. limosum ECO1 strain and ECO2 strain, thereby showing similarity and reproducibility between biological replicates. FIG. 6A shows the H-clustering result, and FIG. 6B shows the PCA analysis result.

FIGS. 7A-7B are a comparison of the transcript expression levels of E. limosum ECO1 strain and ECO2 strain under CO 44% and CO 66% syngas conditions through differentially expressed genes (DEGs) analysis. FIG. 7A shows the number of genes whose transcriptional expression level was increased or decreased significantly (p-value 0.01 or less, $\log_2$ Foldchange of 1 or more-1 or less) in the ECO2 strain compared to the ECO1 strain under the CO 44% syngas condition, and FIG. 7B shows the number of genes whose transcriptional expression level was increased or decreased significantly (p-value 0.01 or less, $\log_2$ Foldchange of 1 or more and −1 or less) in the ECO2 strain compared to the ECO1 strain under the CO 66% syngas condition.

FIGS. 8A-8B show the characteristics of the proteins encoded by genes with significantly increased or decreased transcriptional expression levels (p-value 0.01 or less, $\log_2$ Foldchange of 1 or more-1 or less) in E. limosum ECO1 strain and ECO2 strain under the CO 44% condition and CO 66% syngas condition through Cluster of Orthologous Groups of proteins (COGs) analysis. FIG. 8A shows the categories of characteristics of the proteins with increased or decreased transcriptional expression levels in the ECO2 strain compared to the ECO1 strain under the CO 44% syngas condition, and FIG. 8B shows the categories of characteristics of the proteins with increased or decreased transcriptional expression levels in the ECO2 strain compared to the ECO1 strain under the CO 66% syngas condition.

FIGS. 9A-9B are the transcriptome profiling involved in pyruvate metabolism of ECO1 or ECO2-S6 strains. FIG. 9A is the transcriptome profiling involved in glycolysis/glycogenolysis, TCA and pentose phosphate (PP) pathways, and FIG. 9B is the transcriptome profiling of genes involved in pyruvate oxidation and various amino acid metabolisms.

FIG. 10 is a comparison of the transcriptional expression levels of major metabolic circuits related to the growth of acetogen microorganisms based on transcript data of ECO1 and ECO2 strains under the CO 44% and CO 66% syngas conditions.

FIG. 11 is the energy conservation system of ECO1 or ECO2-S6 and transcriptome profiling of the Wood-Ljungdahl pathway.

FIGS. 12A-12D relate to the development of *E. limosum* producing 2,3-BDO. FIG. 12A shows the design of 2,3-BDO production pathway of *E. limosum* using an inducible promoter, FIG. 12B is a phylogenetic tree of 10 BDH enzymes, FIG. 12C is a measurement result of acetoin or 2,3-BDO production in 9 BDH-expressing *E. limosum* strains, and FIG. 12D is a vector construct for constitutive expression of genes related to the 2,3-BDO metabolic pathway. Error bars represent standard deviations.

FIGS. 13A-13D relate to the production of 2,3-BDO using CO in a recombinant strain. FIG. 13A is the growth profiling and acetate production of WT expressing the 2,3-BDO metabolic pathway under the CO 44% syngas condition, FIG. 13B is growth profiling and acetate production of ECO2-S6 expressing the 2,3-BDO metabolic pathway under the CO 66% syngas condition, FIG. 13C is the production of acetoin and 2,3-BDO from WT expressing the 2,3-BDO metabolic pathway under the CO 44% syngas condition, and FIG. 13D is a result of confirming the production of acetoin and 2,3-BDO from ECO2-S6 expressing the 2,3-BDO metabolic pathway under the CO 66% syngas condition.

DETAILED DESCRIPTION OF PREFERRED EMBODIMENTS

Hereinafter, the present invention will be described in detail by way of Examples and Experimental Examples. However, these Examples and Experimental Examples are given for illustrative purposes only, and the scope of the present invention is not intended to be limited to or by these Examples and Experimental Examples.

Example 1. Materials and Methods

Example 1-1. Media Preparation and Bacterial Cultivation

Wild-type *Eubacterium limosum* ATCC 8486 was obtained from the Leibniz Institute DSMZ-German Collection of Microorganisms and Cell Cultures (DSMZ, Braunschweig, Germany).

The *E. limosum* ECO1 strain was obtained from a previous adaptive laboratory evolution (ALE) study based on wild-type *E. limosum* (Kang S, Song Y, Jin S, Shin J, Bae J, Kim D R, Lee J-K, Kim S C, Cho S and Cho B-K (2020) Adaptive Laboratory Evolution of *Eubacterium limosum* ATCC 8486 on Carbon Monoxide. *Front. Microbiol.* 11:402. doi: 10.3389/fmicb.2020.00402), and the strain was deposited at the Korean Collection of Type Cultures of Korea Research Institute of Bioscience and Biotechnology with Accession No. KCTC 14201BP on Jun. 4, 2020.

All strains were cultivated under strictly anaerobic conditions at 37° C. in a 100 mL modified DSMZ 135 medium. For autotrophic cultivation, a 50 mL headspace was filled with CO 44% syngas (CO 44%, $CO_2$ 22%, $H_2$ 2%, and $N_2$ balance), CO 66% syngas (CO 66%, $CO_2$ 22%, $H_2$ 2%, and $N_2$ balance), CO 60% (CO 60%, and $N_2$ balance), CO 80% (CO 80%, and $N_2$ balance), or CO 100% at a pressure of 200 kPa. For heterotrophic cultivation, 5 $g \cdot L^{-1}$ glucose was added to the modified DSMZ 135 medium.

The wild-type or ECO2 strains were cultivated in 100 ml of DSMZ 135 medium without sodium bicarbonate under CO syngas conditions for CO fermentation. The pre-cultivated microbes were inoculated into a gas-lift fermenter with a 700 mL working volume with the continuous addition of CO syngas. The pH of 6.5 was maintained using 5 N KOH and 1 N HCl during fermentation.

Example 1-2. Adaptive Laboratory Evolution (ALE)

ALE was performed under 66% CO syngas conditions using the ECO1 strain disclosed in Kang S, Song Y, Jin S, Shin J, Bae J, Kim D R, Lee J-K, Kim S C, Cho S and Cho B-K (2020) Adaptive Laboratory Evolution of *Eubacterium limosum* ATCC 8486 on Carbon Monoxide. *Front. Microbiol.* 11:402. doi: 10.3389/fmicb.2020.00402

After inoculating the ECO1 strain, passage transfer was conducted by adjusting the initial inoculation to an optical density (OD) of 0.01. The growth rate was calculated based on the OD value between the inoculation and passage transfer points.

Example 1-3. Metabolite Analysis by High-Performance Liquid Chromatography (HPLC)

Analysis samples were prepared by filtering the cultures with 0.2 µm Minisart® RC15 syringe filters (Sartorius, Göttingen, Germany). All metabolites were detected by an index detector (Waters, Milford, MA, USA) using 0.6 $mL \cdot min^{-1}$ solvent (0.007 N $H_2SO_4$) flow rate.

Example 1-4. Measurement of CO Consumption Rate by Gas Chromatography

CO and $CO_2$ were quantified using a gas chromatography (Shimadzu, Japan) equipped with a ShinCarbon ST Micropaked column (1 mm×2 m, 1/16", 100/120 mesh) (Restek, Bellefonte, PA, USA) and a thermal conductivity detector. Detection was based on a carrier gas (helium or nitrogen gas) at a flow rate of 30 $mL \cdot min^{-1}$. The initial oven temperature was 30° C. for 1 min, and the temperature was increased at a rate of 5° C. min-1 until 100° C. The temperature of the injector and detector was set to 100° C.

Example 1-5. Whole-Genome Re-Sequencing (WGS)

To extract genomic DNA, all strains were prepared under heterotrophic conditions. The cells were then frozen in liquid nitrogen and ground using a mortar and pestle. After treating 600 µL of nuclei lysis solution (Promega, Madison, WI, USA), the samples were incubated at 80° C. for 5 min.

The samples were transferred to ice, and 100 µg·µL$^{-1}$ of RNase A solution (Qiagen, Hilden, Germany) was added. Protein precipitation buffer (Promega, Madison, WI, USA) was used to precipitate proteins in the samples. After incubating for 10 min on ice, the samples were centrifuged at 16,000×g at 4° C. for 10 min. The supernatant was transferred, and ethanol precipitation was performed. Finally, elution buffer was used to dry the pellet, and the genomic DNA concentration was determined using a Qubit™ dsDNA HS Assay kit (Invitrogen, Waltham, MA, USA). A whole-genome re-sequencing (WGS) library was constructed using a TruSeq Nano DNA library prep kit (Illumina, La Jolla, CA, USA), and library concentration was quantified using a Qubit™ dsDNA HS Assay kit. Sequencing was performed using the Hiseq2500 rapid-run mode in a 50-cycle single-ended reaction (Illumina, La Jolla, CA, USA).

All WGS data were analyzed using the CLC Genomics Workbench 6.5.1 (CLC bio, Aarhus, Denmark). Sequencing reads were mapped to the reference genome of *E. limosum* ATCC 8486 (NZ_CP CP019962.1) using mapping parameters (mismatch cost=2, insertion cost=3, deletion cost=3, length fraction=0.9, and similarity fraction, =0.9). Variants were analyzed using a quality-based variant detection tool in the CLC workbench with the following parameters: neighborhood radius, 5; maximum gap and mismatch count, 5; minimum 157 neighborhood quality, 30; minimum central quality, 30; minimum coverage, 10; minimum 158 variant frequency, 10%; maximum expected alleles, 4; nonspecific matches, ignore; and genetic 159 code, bacterial and plant plastid. The WGS data generated in this study are available in the EMBL European Nucleotide Archive (ENA) under accession number PRJEB51838.

Example 1-6. Transcriptome Analysis

*E. limosum* strains were injected with CO syngas and sampled at the mid-exponential stage (OD$_{600\ nm}$≈1.0) by centrifugation at 10,000×g at 4° C. for 10 min. The pellets were resuspended by 500 µL of lysis buffer (20 mM Tris-HCl pH 7.4, 140 mM NaCl, 5 mM MgCl$_2$, and 20% of Triton X-100), immediately frozen using liquid nitrogen, followed by grinding using a mortar and pestle. Total RNA was isolated using 600 µL of TRIzol reagent (Thermo Fisher Scientific, Waltham, MA, USA). To eliminate genomic DNA, DNase I (NEB, Ipswich, MA, USA) was added to 1 µg of total RNA and incubated at 37° C. for 10 min. To deplete ribosomal RNA (rRNA) based on the RiboRid method disclosed in Choe D, Szubin R, Poudel S, Sastry A, Song Y, Lee Y, et al. (2021) RiboRid: A low cost, advanced, and ultra-efficient method to remove ribosomal RNA for bacterial transcriptomics. PLOS Genet 17 (9): e1009821, 15 µL hybridase complement buffer (90 mM Tris-HCl (pH 7.5) and 200 mM KCl) was added to DNase-treated RNA samples and incubated at 75° C. for 10 min to inactivate DNase I. Anti-rRNA oligo DNA mix (5 µmol·µL$^{-1}$) and 2 µL of 50 mM MgCl$_2$ were added to the samples, heated to 90° C. for 1 s, and cooled to 65° C. using a thermocycler. When the temperature of the samples in the thermocycler reached 65° C., 2 µL of Hybridase Thermostable RNase H (Lucigen, Middleton, WI, USA) pre-warmed at room temperature (about 25° C.) was added to the samples and incubated at 65° C. for 20 min, 90° C. for 1 s, and 65° C. for 10 min. Then, long RNA (>200 nt) in samples was isolated using the RNA Clean and Concentrator Kit (Zymo Research, Orange, CA, USA). Finally, DNase I reaction was performed by incubating the eluted samples at 25° C., 30° C., 35° C., 40° C., and 45° C. using a thermocycler. Then, the rRNA-depleted samples were purified using the RNA Clean and Concentrator Kit.

RNA-seq libraries were constructed using the TruSeq Stranded mRNA Library Prep Kit (Illumina) according to the manufacturer's instructions. RNA-seq was performed in the Hiseq2500 rapid-run mode as a 50-cycle single-ended reaction. All RNA-seq data were analyzed using CLC Genomics Workbench 6.5.1. Sequencing reads were mapped to the reference genome of *E. limosum* ATCC 8486 (NZ_CP CP019962.1) using mapping parameters (mismatch cost=2, insertion cost=3, deletion cost=3, length fraction=0.9, and similarity fraction=0.9). Raw read counts per gene were calculated using the CLC program to obtain uniquely mapped reads from the sequencing results. Finally, DEseq2 normalization was conducted using read counts per gene (M. I. Love, W. Huber, S. Anders, Moderated estimation of fold change and dispersion for RNA-seq data with DESeq2, *Genome Biol* 15 (12) (2014) 550). The RNA-seq data generated in this study are available in the EMBL European Nucleotide Archive (ENA) under accession number PRJEB51838.

Example 1-7. Vector Construction

A modified pJIR750 vector was prepared as disclosed in J. Shin, S. Kang, Y. Song, S. Jin, J. S. Lee, J. K. Lee, D. R. Kim, S. C. Kim, S. Cho, B. K. Cho, Genome Engineering of *Eubacterium limosum* Using Expanded Genetic Tools and the CRISPR-Cas9 System, *ACS Synth Biol* 8 (9) (2019) 2059-2068 and S. Kang, Y. Song, S. Jin, J. Shin, J. Bae, D. R. Kim, J. K. Lee, S. C. Kim, S. Cho, B. K. Cho, Adaptive Laboratory Evolution of *Eubacterium limosum* ATCC 8486 on Carbon Monoxide, *Front Microbiol* 11 (2020) 402, and digested with XhoI and XbaI for linearization. To construct the CODH/ACS overexpression vector, DNA fragments encoding CODH/ACS clusters from *E. limosum* wild-type or ECO2 strain were amplified using the primers Inf_CODH_1653_F with the Inf_CODH_1655_R pair.

For site-directed mutagenesis, DNA fragments were amplified using the primers Inf_CODH_1653_F with Inf_SDM_475_R pairs, or Inf_SDM_475_F with Inf_CODH_1655_R pairs. The PCR templates with the linearized pJIR750 vector were assembled using the In-Fusion HD cloning kit (TakaRa, Japan). Finally, all plasmids were transformed into *Escherichia coli* DH5a competent cells (Enzynomics, Daejeon, South Korea) and colonies were selected on LB agar plates containing 30 µg·mL$^{-1}$ of chloramphenicol.

To construct the 2,3-butanediol dehydrogenase (BDH) enzyme screening vector, each DNA fragment of the pTet, alsS, and alsD genes from previously constructed plasmids was amplified using PCR with the primer pairs listed in Table 3. Nine BDH enzymes were synthesized using *E. limosum* ATCC 8486 codon optimization (IDT, Coralville, IA, USA). To regulate the expression of BDHs, the promoter/UTR region in ELIM_c1476 was amplified using the primer pEL1476_1st_F and pEL1476_1st_R pairs. To construct the BDH screening vector, all PCR templates with the linearized pJIR750 vector were assembled using the In-Fusion HD cloning kit.

To construct the pJIR750::alsSD::Cbbdh vector, each promoter/UTR in *E. limosum* was amplified using the PCR primers Inf_p0077_u1121_F with Inf_p0077_u1121_R pair or Inf_p1121_u1121_F with Inf_p1121_u1121_R pair. To construct the pJIR750::alsSD vector, the alsS and alsD were amplified using the PCR primers Inf_alsS_p0077_F with Inf_alsS_R or Inf_alsD_p1121_F with Inf_alsD_R pairs. These DNA fragments, including alsS, p0077 parts, p1121 parts, and alsD, with linearized pJIR750 vector (digested by SacI and SalI), were assembled using the In-Fusion HD cloning kit. To insert the BDH template into the pJIR750::alsSD vector, the vector was digested with the SalI enzyme. The p1476::Cbbdh template and CD0164 terminator in the pMTL82254 vector were prepared using pEL1476_EcoRI_XhoI_F with SalI_term_p1476_BDHs_R primer pairs or SalI_term_p1476_BDHs_F with XhoI_term primer pairs, respectively. Both BDH and terminator templates with linearized pJIR750: alsSD (digested by SalI) vectors were assembled using the In-Fusion HD cloning kit. All plasmids were transformed into E. coli DH5a competent cells, and colonies were selected on LB agar plates containing 30 μg·mL$^{-1}$ of chloramphenicol.

The information of the plasmids and primers used is shown in Table 3 below.

TABLE 3

| Previous works | Vector names | Note |
|---|---|---|
| Shin et al., 2020, ACS Synthetic Biology | pJIR750ai<br>pJIR750 modified | This plasmid were purchased from Sigma-Aldrich pJIR750ai digested by PvuI and self ligation using T4 DNA ligase |
| Kang et al., 2020, Frontiers in Microbiology | pMTL82254 | We amplification of CD0164, Cpa fdx terminator region to using termination |

| Experiments | Primer Names | Sequence (5' to 3') |
|---|---|---|
| CODH/ACS Over-expression | Inf_CODH_1653_F | ccATGATACGAATTCCTCGAGAAGAAGTTAATAAAAAAATAAGCCCCTA |
| | Inf_CODH_1655_R | ttttatTAATCTAGAAAGCTTAATAATTCCTCCAAACTTTTATAATTTA |
| | Inf_SDM_475_F | ACGTACGTGTAGCAAGACTGAACTCACTGACAGA |
| | Inf_SDM_475_R | CAGTCTTGCTACACGTACGTTGTAGATTGGTC |
| BDH screening | pEL1476_EcoRI_XhoI_F | tacGAATTCCTCGAGAAAGAAGATTTGCTAAAGAAAGAG |
| | pEL1476_1st_R | GAAAACCTCTTTCAACGAAATAAG |
| | bdhA_C.beijerinckii_F | TTATTTCGTTGAAAGAGGTTTTCAACCATGGTGAAGGCTGCTCTTTG |
| | bdhA_C.beijerinckii_R | AACTCGTCTCAAAGTCTTAGGCGGCCGCTCTAGATTAata |
| | bdhA_B.sutilis_F | TTATTTCGTTGAAAGAGGTTTTCAACCATGGTGAAGGCCGCACGGTG |
| | bdhA_B.sutilis_R | TCCTGGTCCGGCCCAATTAGGCGGCCGCTCTAGATTAata |
| | bdh_L.lactics_F | TTATTTCGTTGAAAGAGGTTTTCAACCATGGTGCGTGCGGCCCGTTT |
| | bdh_L.lactics_R | CGACCGGCAAGGGCCTGTAAGGCGGCCGCTCTAGATTAat |
| | adh_T.brockii_F | TTATTTCGTTGAAAGAGGTTTTCAACCATGGTGAAAGGCTTTGCGAT |
| | adh_T.brockii_R | CTGTGGTCATTCTCGCTTAAGGCGGCCGCTCTAGATTAat |
| | budC_B.licheniformis_F | TTATTTCGTTGAAAGAGGTTTTCAACCATGGTGTCAAAAGTGTCAGG |
| | budC_B.licheniformis_R | GGGGAATGGTGTTCAACTAAGCGGCCGCTCTAGATTAata |
| | budC_K.aerogenes_F | TTATTTCGTTGAAAGAGGTTTTCAACCATGGTGAAAAAGGTGGCACT |
| | budC_K.aerogenes_R | GTGGCATGGTCTTTAATTAGGGCGGCCGCTCTAGATTAat |
| | budC_K.pneumoniae_F | TTATTTCGTTGAAAGAGGTTTTCAACCATGGTGAAAAAAGTAGCGCT |
| | budC_K.pneumoniae_R | GGGGAATGGTGTTCAACTAAGCGGCCGCTCTAGATTAat |
| | budC_K.oxytoca_F | TTATTTCGTTGAAAGAGGTTTTCAACCATGGTGGCGATTGAGAATAA |
| | budC_K.oxytoca_R | GAGGCATCGTCTATCGGTAAGCGGCCGCTCTAGATTAat |
| | bdh_C.autoethanogenum_F | TTATTTCGTTGAAAGAGGTTTTCAACCATGGTGAAAGCTGTATTGTG |
| | bdh_C.autoethanogenum_R | CTGACAAATCCTTATTGTAAGCGGCCGCTCTAGATTAata |
| | 04_tetRO1_F | CGGAGCTCGTAATTCTCTATCACTG |
| | 04_tetRO1_R | CGAGATCTatgaacaaagatattatACTCTATC |
| | 01_U3471_alsS_1st_F | TATGGAATAGAGGTTAAAAACCATGGTGTTGACAAAAGCAAC |

TABLE 3-continued

| | | |
|---|---|---|
| | 01_U3471_alsS_2nd_F | CCGAGCTCGCAGATCTGATTTTATTTGATTTAT GGAATAGAGGTT |
| | 01_alsS_SalI_R | CCGTCGACCTAGAGAGCTTTCGTTTTCA |
| | 02_SalI_U0077_alsD_SdaI_F | CCGTCGACAACTAAACGCAGGAGGTTTACACC ATGGAAACTAATAGC |
| | 02_alsD_R | GCGGCTGAGGGTTAGCCTGCAGGTCACTTAC TAAGAATT |
| Constitutive expression of 2,3-BDO pathway | alsS_R | ATGATTACGAATTCGAGCTCCTAGAGAGCTTT CGTTTTCATGAGTTCC |
| | Inf_alsS_F | TTGTTTCAAGGAGGAActcgaGATGTTGACAAAA GCAACAAAAGAACAAAAATC |
| | Inf_P0077_U1121_1st_F | GACGTTCTGAGCTCTCTTATTATTATACCACAT TTCGGCTGAGCCTAA |
| | Inf_U1121_P0077_2nd_F | cgagTTCCTCCTTGAAACAAGACGTTCTGAGCT CTCTTATTATTA |
| | alsS_P0077_U1121_F3 | CCGGTAAATGGGATCCATGAAGGAGGGCATC TTCGTG |
| | alsD_P1121_U1121_F | ACATCtcgagGGATCCCATTTACCGGGCCAAGC |
| | alsS_P_U1121_univ | TTGTCAACATCtcgagTTCCTCCTTGAAACAAGA CGTTCTGAG |
| | alsD_F | CGGTACCCGGGGATCCAcgcgtaTGGAAACTAA TAGCTCGTGCGATTG |
| | alsD_R | ATGCCTGCAGGTCGACCTAACCCTCAGCCGC ACGGATAG |
| | EcoRI_term | GTCACTTACTAAGAATTCgcaagaccgatcgggccc |
| | XhoI_term | TAGCAAATCTTCTTTCTCGAGggtcatagctgtttcctg at |
| | SalI_term_p1476_BDHs_F | AGGTCGACGTCACTTACTAAGAATTCgcaagac |
| | SalI_term_p1476_BDHs_R | aggtcgacATGCGGATCCTAAataaaaataagaagc |
| | NotI_XbaI_F | TTAGGCGGCCGCTCTAGATTA |

Example 1-8. Plasmid Transformation to *E. limosum*

*E. limosum* transformants were prepared using electro-transformation methods, using a modified protocol disclosed in J. Shin, S. Kang, Y. Song, S. Jin, J. S. Lee, J. K. Lee, D. R. Kim, S. C. Kim, S. Cho, B. K. Cho, Genome Engineering of *Eubacterium limosum* Using Expanded Genetic Tools and the CRISPR-Cas9 System, *ACS Synth Biol* 8 (9) (2019) 2059-2068 and S. Kang, Y. Song, S. Jin, J. Shin, J. Bae, D. R. Kim, J. K. Lee, S. C. Kim, S. Cho, B. K. Cho, Adaptive Laboratory Evolution of *Eubacterium limosum* ATCC 8486 on Carbon Monoxide, Front Microbiol 11 (2020) 402. To prepare electrocompetent cells, *E. limosum* WT or ECO2 strains were cultured in 100 mL of DSM 135 medium under heterotrophic conditions. The cells were harvested in the exponential phase (OD approximately 0.5) by centrifugation at 10,000×g at 4° C. for 15 min. The pellets were washed with 270 mM sucrose buffer (pH 6.0), and the process was repeated. Finally, the pellets were resuspended in 500 μL of sucrose buffer and mixed with 1.0 μg plasmids. The mixture samples were transferred to a 0.1 cm-gap Gene Pulser cuvette (Bio-Rad, Hercules, CA, USA). Thereafter, the mixture samples were pulsed at 2.0 kV and immediately resuspended with 0.9 mL of reinforced clostridial medium. The resuspended samples were incubated at 37° C. for 16 h and spread on reinforced clostridial medium agar plates containing 15 μg·mL$^{-1}$ thiamphenicol.

Example 1-9. CO Gas Fermentation

The gas fermenter used in the present invention was a 1 L scale gas-lift tower fermentor (700 mL of working volume) consisting of a cylinder (300 mm×ϕ65) and a draft tube (160 mm×ϕ30) (Fermentec Co., Cheongju, Republic Korea). The medium used was a 700 mL of modified DSM135 medium with controlled composition (2 g·L$^{-1}$ yeast extract, 2 g·L$^{-1}$ NH$_4$Cl, 0.1 g·L$^{-1}$ MgSO$_4$·7H$_2$O, 0.45 g·L$^{-1}$ cysteine-HCl, 2.35 g·L$^{-1}$ NaCl, 7.5 μg·mL$^{-1}$ Thiamphenicol), and 14 mL of trace element solution (1.5 g·L$^{-1}$ nitrilotriacetic acid, 3.0 g·L$^{-1}$ MgSO$_4$·7H$_2$O, 0.5 g·L$^{-1}$ MnSO$_4$·H$_2$O, 1.0 g·L$^{-1}$ NaCl, 0.1 g·L$^{-1}$ FeSO$_4$·7H$_2$O, 0.1 g·L$^{-1}$ CaCl$_2$), 0.1 g·L$^{-1}$ CoCl$_2$·6H$_2$O, 137 mg·L$^{-1}$ ZnSO$_4$·7H$_2$O, 10 mg·L$^{-1}$ CuSO$_4$·5H$_2$O, 20 mg·L$^{-1}$ KAl(SO$_4$)$_2$·12H$_2$O, 10 mg·L$^{-1}$ H$_3$BO$_3$, 10 mg·L$^{-1}$ Na$_2$MO$_4$·2H$_2$O), 7 mL of phosphate buffer (pH 7.0), and 7 mL of Wolfe's vitamin stock solution (4 mg·L$^{-1}$ biotin, 4 mg·L$^{-1}$ folic acid, 20 mg·L$^{-1}$ pyridoxine-HCl, 10 mg·L$^{-1}$ thiamine-HCl, 10 mg·L$^{-1}$ riboflavin, 10 mg·L$^{-1}$ nicotinic acid, 10 mg·L$^{-1}$ pantothenate, 0.2 mg·L$^{-1}$ vitamin B12, 10 mg·L$^{-1}$ p-aminobenzoic acid, 10 mg·L$^{-1}$ lipoic acid) were added thereto. The microorganisms for gas fermentations were inoculated at an O.D value of 0.1. CO 44% or CO 66% syngas was used for gas fermentation and supplied into the cylinder using a 0.2 mm gas sparger at a gas flow of 0.05 L·min$^{-1}$. The pH during the gas fermentation was monitored using a pH probe (InPro3253i/SG/120, Mettler Toledo, Columbus, USA), and the fermentation was carried out by adjusting the pH to 6.5 using 5 N KOH and 1 N HCl. The cultivation temperature was maintained at 37° C. by connecting a water bath circulator (DAIHAN, Seoul, Republic Korea).

Example 2. Experimental Results

Example 2-1. Adaptive Laboratory Evolution (ALE) of ECO1 Strain (KCTC 14201BP) to Improve CO Tolerance

*E. limosum* ECO1 strain was a strain obtained from a previous adaptive laboratory evolution (ALE) study based on wild-type *E. limosum* (Kang S, Song Y, Jin S, Shin J, Bae J, Kim D R, Lee J-K, Kim S C, Cho S and Cho B-K (2020) Adaptive Laboratory Evolution of *Eubacterium limosum* ATCC 8486 on Carbon Monoxide. *Front. Microbiol.* 11:402. doi: 10.3389/fmicb.2020.00402), and the strain was deposited at the Korean Collection of Type Cultures of Korea Research Institute of Bioscience and Biotechnology with Accession No. KCTC 14201BP on Jun. 4, 2020.

To test the capability of strains to grow under more than 60% CO syngas conditions, both the ECO1 and wild-type strains were cultured using syngas containing 66% CO.

The biomass of the ECO1 strain was 2-fold higher than that of the wild-type strain under these conditions (FIG. 1a). This result indicates that the ECO1 strain grown under 66% CO syngas conditions can only grow at 35% of the biomass under 44% CO syngas conditions. The growth rates of the ECO1 and wild-type strains dropped from 0.095 h$^{-1}$ and 0.07 h$^{-1}$ at 44% CO to 0.022 h$^{-1}$ and 0.014 h$^{-1}$ at 66% CO, respectively (FIG. 1b).

Although it was almost impossible for the wild-type strain to proliferate under 66% CO syngas conditions, the ECO1 strain grew slowly under these conditions. WGS results revealed that the A97E mutation in the acsA gene (ELIM_c1653), which causes the phenotype of the ECO1 strain, existed in approximately 30% of the total ALE population. This mutation frequency indicates that the acsA mutants in the ECO1 population rapidly oxidize CO, causing reduction of the CO concentration in the growth medium (Kang S, Song Y, Jin S, Shin J, Bae J, Kim D R, Lee J-K, Kim S C, Cho S and Cho B-K (2020) Adaptive Laboratory Evolution of *Eubacterium limosum* ATCC 8486 on Carbon Monoxide. *Front. Microbiol.* 11:402. doi: 10.3389/fmicb.2020.00402). Thus, it was assumed that this reduction of CO level in selection pressure was not sufficient to complete the ALE. To overcome this, the next round of ALE of the ECO1 population was performed under 66% CO syngas conditions. Each passage was transferred to a fresh medium by adjusting the inoculation to OD of 0.01 at 48 h intervals. Growth rate fluctuation was observed around 150th generations, after which the growth rate was maintained at a 1.5-fold increase compared to that of the first generation. However, cell growth deviated from the exponential phase after approximately 200th generations; hence, the time interval for passage transfer was reduced from 48 to 36 h after 245th generations. Subsequently, no further change in the growth rate was observed, even after passage transfer was continued, thus, the ALE was completed at approximately 390th generations (FIG. 1c). The cell population in the final generation was named as the ECO2 population.

To confirm the cell growth improvement of the ECO2 population, the growth of the wild-type, ECO1, and ECO2 populations was measured under CO 66% syngas growth conditions.

As a result, the final biomass of the ECO2 population was 7.93- and 4.38-fold higher than that of the wild-type and ECO1 strains, respectively, under the growth conditions (FIG. 1d). Furthermore, the growth rate of the ECO2 population was 0.11 h$^{-1}$, which was 7.86- and 5.0-fold higher compared to wild-type and ECO1 strains, respectively. Thus, the growth rate of ECO2 population was about 6.1-fold higher than WT strain under the CO 60% condition. In addition, the population exhibited a high tolerance to CO where its growth rate was approximately 2-fold or higher even at 80% and 100% CO concentrations compared to that of the wild-type strain (FIG. 1e).

Example 2-2. Determination of ALE-Driven Mutations in ECO2 Strain

Since the ECO2 population showed various genotypes (i.e., mutations), the present inventors made an attempt to determine the driver mutations for elucidating CO tolerance.

Ten single colonies (ECO2-S1-S10) were isolated from the population and their growth rates were measured. As a result, the ECO2-S6 and ECO2-S8 strains showed the most similar phenotype to the ECO2 population (FIG. 2a).

To determine the driver mutations that induced phenotypic changes in the ECO2 population under high CO syngas conditions, the genomes of the ECO2 population and ten single colonies were re-sequenced.

After extracting genomic DNA, sequencing libraries were constructed and sequenced using the Illumina sequencing platform (Experimental section), resulting in the identification of 13 mutations (Table 4).

TABLE 4

| Strains | Locus tag | Gene | Mutation | Type | AA change | Description |
|---|---|---|---|---|---|---|
| Population | ELIM_c1655 | acsB | A1907G | SNV | His636Arg | CODH/ACS complex subunit beta |
| S3 | ELIM_c1653 | acsA | C275T | SNV | Ala92Val | CODH catalytic subunit |
| S6 | ELIM_c1655 | acsB | A1907G | SNV | His636Arg | CODH/ACS complex subunit beta |
| S7 | ELIM_c1655 | acsB | A1907G | SNV | His636Arg | CODH/ACS complex subunit beta |
| | ELIM c2589 | — | G148A | SNV | Asp50Asn | hypothetical protein |
| | ELIM_c2589 | — | C195T | SNV | | hypothetical protein |
| S8 | ELIM c1655 | acsB | A1907G | SNV | His636Arg | CODH/ACS complex subunit beta |

The ECO2-S6 and ECO2-S8 strains showed only the A1907G mutation in the acsB gene (ELIM_c1655), which changed the amino acid residue (H636R) of the acsB protein, encoding ACS of the CODH/ACS complex.

Because ACS plays a crucial role in synthesizing acetyl-CoA by delivering CO molecules to methyl-CoFeSP, it was hypothesized that the H636R mutation is the key driver mutation that induces phenotypic changes in the ECO2 population. In addition, if the rapid growth rate and high biomass formation of the ECO2 population under the 66% CO syngas condition were caused by a mutation in ACS, the CO gas consumption rate of the ECO2 population would also have increased under these conditions.

To prove this, the CO gas consumption of the ECO2-S6 strain, which has a genetic mutation in acsB and the most similar phenotype to the ECO2 population, was quantified by gas chromatography.

The biomass growth rate was increased about 4.0-fold higher in the ECO2-S6 strain under the CO 66% syngas condition compared to the ECO1 strain (FIG. 4a), and the ECO1 strain showed a maximum CO gas consumption rate of 0.032 mmol·h$^{-1}$, while the ECO2-S6 strain showed a maximum of 0.081 mmol-h$^{-1}$, and accordingly, the CO gas consumption rate was increased about 2.5-fold higher in the ECO2-S6 strain under 66% CO syngas condition compared to the ECO1 strain (FIGS. 2b and 4b).

Consequently, the ECO2-S6 strain with the mutation in the acsB gene showed a high CO gas consumption, which increased CO tolerance, thereby showing a high growth rate under the 66% CO syngas condition.

The ECO2-S6 strain was deposited at the Korean Collection for Type Cultures of Korea Research Institute of Bioscience and Biotechnology, an International Depositary Authority, under Budapest Treaty on Jul. 14, 2022 with Accession No. KCTC15034BP.

Example 2-3. Effect of H636R Mutation on ACS Function

The ACS is composed of three domains (ACS Catal. 2020, 10, 17, 9741-9746 Publication Date: Aug. 10, 2020. doi.org/10.1021/acscatal.0c03033). Domain 1, where the CO gas tunnel is located, is connected to the CODH. Domain 3 has an A-cluster, where acetyl-CoA is synthesized using CO produced by CODH from $CO_2$, coenzyme A (CoA-SH), and methyl group held by cobalamin in a corrinoid/FeS protein (CoFeSP). Methyl-CoFeSP is the final product of the methyl branch of the WL pathway. Domain 2 is a bridge that connects domain 1 with domain 3. The CODH/ACS complex operates via a conformational change in the CO tunnel between its open and closed forms. The open conformation led to the opening of the CO gas tunnel from domain 1 to the A-cluster in domain 3, resulting in the transfer of CO from CODH (FIG. 3a).

To elucidate the mechanism by which the H636R mutation in ACS changed the function of the CODH/ACS complex, the structural differences between the wild-type and mutant proteins were observed.

The ACS structure was predicted using AlphaFold2. When the predicted structure with the CODH/ACS structure data (6×5K) of Morella thermoacetica were compared, the acsB WT model overlapped with the reference structure (Ca-RMSD ~1.91 Å) (FIG. 5a). The model was then used as a reference structure for comparison with the predicted structure of the ACS mutant.

As a result, in the case of the ACS mutant, it seems that hydrogen bonding was possible as $H_{636}$ was changed to R636 and was located close to D475 by approximately 2.5 Å (FIG. 5b). Therefore, as the distance between domains 2 and 3 decreased due to the interaction between R636 and D475, the probability of conformational change of the CO tunnel to an open form increased (FIG. 3b). The structural models suggested that the position of domain 3 was biased toward domain 2 in the ACS mutant compared to that in wild-type ACS (FIG. 5c).

Based on these results, it was hypothesized that the interaction between R636 and D475 caused functional changes in ACS. To test this hypothesis, wild-type and mutated CODH/ACS were inserted into the pJIR750 vector and transformed into wild-type E. limosum. In addition, both D475 and D476 in the ACS mutant changed to D475V and D476A (FIG. 3c). To alleviate the effect of antibiotics on growth inhibition, growth profiling was performed under mixotrophic conditions by adding 5 g·L$^{-1}$ of glucose to the media with 66% CO syngas.

For expressing mutant CODH/ACS (H636R), the maximum OD value was significantly higher than that of the wild-type CODH/ACS (FIG. 3d). Interestingly, strains expressing D475V or D476A mutants showed growth similar to that of the wild-type strain under 66% CO mixotroph conditions (FIG. 3d). These results suggest that the H636R mutation in ACS was a driver mutation for the phenotype of the ECO2-S6 and ECO2-S8 strains, in which the interaction between R636 and D475 increased their high CO tolerance.

Example 2-4. Transcriptome Analysis of ECO2-S6 Strain Under CO Syngas Conditions To investigate the changes in the transcription levels of ECO2-S6, RNA sequencing (RNA-seq) was performed under 44% and 66% CO syngas conditions (Experimental section).

RNA-seq data were obtained using the Illumina platform, obtaining at least $1.0 \times 10^7$ sequencing reads with more than×150 coverage in the E. limosum reference genome. DESeq2 normalization was performed using uniquely mapped reads. RNA-seq results were grouped between biological replicates using H-clustering and PCA (FIGS. 6a and 6b). The RNA-seq results were then normalized to the ECO1 results, and the normalized results were cut-off with an adjusted p-value of 0.01 or less, log 2 FoldChange ≥1, and −1 or less.

Under 44% CO syngas conditions, the RNA-seq results of the ECO2-S6 strain showed that 335 and 413 genes were up-regulated or down-regulated, respectively (FIG. 7a). In contrast, under 66% CO syngas conditions, 500 and 536 genes in the ECO2-S6 strain were up-regulated or down-regulated, respectively, compared to the ECO1 strain (FIG. 7b).

Next, genes that changed significantly in each condition were classified according to COG (Clusters of Orthologous Groups) to determine the protein functions altered in the ECO2-S6 strain. Unlike 44% CO syngas conditions, J (translation, ribosomal structure, and biogenesis) and E (amino acid transport and metabolism) categories of the ECO2-S6 strain were up-regulated compared to those of the ECO1 strain under 66% CO syngas conditions (FIGS. 8a and 8b). The amino acid biosynthesis pathways for valine, leucine, and isoleucine were also up-regulated (FIG. 9a).

To confirm whether such transcriptional changes were caused by the difference in the growth rates of ECO1 and ECO2-S6 strains, it was confirmed that there was almost no difference in gene expression level in glycolysis and TCA related to the growth of acetogen microorganisms, whereas there was a difference in gene expression of the Wood-Ljungdahl pathway, ribosome, and fatty acid biosynthesis related genes, which are related to autotrophic growth, between the ECO2 strain and the ECO1 strain (FIG. 10).

Thus, the transcription levels of genes involved in acetogenesis were compared. The expression levels of genes encoding the methyl branch in ECO2-S6 increased by 0.75- or 1.46-fold compared to the ECO1 strain under 44% or 66% CO syngas conditions, respectively. In contrast, the transcription levels of genes encoding the carbonyl branch in ECO2-S6 were down-regulated to −0.96- or −0.91-fold under both conditions (FIG. 11). This transcriptional change suggested that the transcription levels of genes encoding the methyl branch increased to obtain methyl-CoFeSP, the substrate of the ACS protein, rapidly produced by the increased enzymatic activity of acetyl-CoA synthesis in the ECO2-S6 strain.

In addition, since CODH/ACS activity was high in the ECO2-S6 strain, the transcription levels of genes encoding the carbonyl branch were decreased, balancing the methyl and carbonyl branches. Energy conservation systems, such as the Rnf complex and ATP synthase, were up-regulated in the ECO2-S6 strain compared to those in the ECO1 strain. The transcription levels of the Rnf complex increased by 0.7- to 1.5-fold compared to the ECO1 strain under CO 66% syngas conditions. For ATP synthase, E. limosum has two gene clusters encoding V-type ATP synthase. Interestingly, under 66% CO syngas conditions, the transcription level of the second ATP synthase increased approximately 1.2- to 2.2-fold. Because the expression level of the first cluster was already high, the expression of the second cluster increased significantly in the ECO2-S6 strain under 66% CO syngas conditions.

Consequently, the transcriptome in the ECO2-S6 strain suggested that the strain regulated the transcriptional balance of the WL pathway by increasing the transcription level of the methyl branch and decreasing that of the carbonyl branch according to the CODH/ACS activity under 66% CO syngas conditions. This result indicates that the phenotype of ECO2-S6 grown under 66% CO syngas conditions was affected by the H636R mutation in ACS and was not affected by increasing transcription levels of the CODH/ACS complex. In addition, it was found that the transcription level of the energy conservation system increased following increased CO conversion.

Example 2-5. Development of 2,3-BDO-Producing Strain under 66% CO Syngas Conditions The ECO2-S6 strain showed high biomass formation under 66% CO syngas conditions. The transcription levels of the genes encoding pyruvate metabolism were also increased. Therefore, it was assumed that converting pyruvate to other value-added chemicals would be advantageous in the ECO2-S6 strain. Acetoin was previously produced from *E. limosum* using a vector encoding the acetoin biosynthesis pathway in the previous study. Accordingly, in this Example, it was attempted to express 2,3-butanediol dehydrogenase (BDH) using a Tet-inducible promoter to produce 2,3-BDO using CO as a carbon source (FIG. 12a).

Unlike acetoin, because one molecule of NAD (P) H is required to convert acetoin to 2,3-BDO, a suitable BDH protein was screened in *E. limosum*. Subsequently, the BDH protein sequences in ten species capable of producing 2,3-BDO as a native product were compared. The BDH sequences were divided into two groups. The first group had low molecular weight BDH proteins (budC) with approximately 260 aa (27 kDa), comprising mainly *Klebsiella pneumoniae*. Another group had high molecular weight BDH proteins (bdh) with approximately 360 aa (39 kDa), comprising mainly *Clostridium autoethanogenum* (FIG. 12b). Since the amino acid sequences of the BDHs of *Enterobacter cloacae* and *K. pneumoniae* were the same, nine BDHs were tested in *E. limosum*. A 2,3-BDO biosynthesis pathway connecting nine BDH enzymes were constructed, followed by transformation into the wild-type strain. Each strain was then cultured under heterotrophic conditions. The highest BDO titer was determined in *E. limosum* expressing *Clostridium beijerinckii* BDH, which was used to develop a 2,3-BDO producing strain (FIG. 12c). To construct a strain capable of stably producing 2,3-BDO from CO syngas, the 2,3-BDO biosynthesis pathway was constructed using the promoter/UTR parts of *E. limosum* (FIG. 12d). The final vector was transformed into wild-type and ECO2-S6 strains.

To compare the biomass formation and 2,3-BDO production levels of the engineered strains, gas fermentation was performed using a 1 L scale gas-lift fermenter. For the WT strain, fermentation was performed using 44% CO syngas for approximately 30 days. Acetate was produced at approximately 0.66 mg·$L^{-1}h^{-1}$, and the final titer was approximately 0.55 g·$L^{-1}$ (FIG. 13a). For 2,3-BDO, about 0.40 mg·$L^{-1}h^{-1}$ was produced, and the final titer was approximately 0.3 g·$L^{-1}$ (FIG. 13b). In contrast, the ECO2-S6 strain was cultured under 66% CO syngas for approximately 30 days. Cell growth reached approximately at 2.5 OD, which was 2.1-fold higher than that of the WT strain. Acetate was produced at approximately 16.21 mg·$L^{-1}h^{-1}$, and the final titer was 11.7 g·$L^{-1}$ (FIG. 13c). For acetate, 24.8-fold productivity and 23.6-fold titer were increased in the ECO2-S6 strain compared to those in the wild-type strain. In particular, 2,3-BDO production in the ECO2-S6 strain having the highest titer of 1.37 g·$L^{-1}$ was produced at 2.60 mg·$L^{-1}h^{-1}$ (FIG. 13d). This result showed 4.5-fold higher productivity and 46.5-fold higher production amount than the WT strain.

In summary, the *E. limosum* ECO2-S6 strain with improved CO tolerance through ALE at a high concentration of CO was obtained. This strain improved the function of CODH/ACS through H636R mutations in ACS, resulting in rapid CO conversion to generate biomass. In addition, when the fed-batch CO fermentation was used by introducing the 2,3-BDO biosynthesis pathway into the evolved ECO2-S6 strain, 1.37 g·$L^{-1}$ of 2,3-BDO was produced at 2.60 mg·$L^-_1h^{-1}$ of productivity. Therefore, it can be seen that the ACS H636R mutation of the present invention increases the CODH/ACS activity to impart CO tolerance to the strain and can be effectively used for the production of biomass.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. The scope of the present invention is therefore indicated by the appended claims rather than by the foregoing description. All changes which come within the meaning and range of equivalency of the claims are to be embraced within the scope of the present invention.

[Deposition Nos.]
Depository Institution: Korea Research Institute of Bioscience and Biotechnology
Accession No.: KCTC 14201BP
Deposition Date: 20200604
Depository Institution: Korea Research Institute of Bioscience and Biotechnology
Accession No.: KCTC 15034BP
Deposition Date: 20220714

The invention claimed is:

1. An acetyl-CoA synthase variant consisting of SEQ ID NO: 1, in which histidine at position 636 from the N-terminus of SEQ ID NO: 1 is substituted with arginine.

2. The acetyl-CoA synthase of claim 1, wherein the variant consists of SEQ ID NO: 3.

3. The acetyl-CoA synthase of claim 1, wherein the variant is encoded by a polynucleotide in which adenine (A) at position 1907 of the acsB gene consisting of SEQ ID NO: 2 is substituted with guanine (G).

4. The acetyl-CoA synthase of claim 1, wherein the variant is encoded by a polynucleotide consisting of SEQ ID NO: 4.

5. The acetyl-CoA synthase of claim 1, wherein the amino acids at positions 475 and 476 from the N-terminus of the variant are aspartic acid (D).

6. A microorganism comprising the acetyl-CoA synthase variant of claim 1, wherein the microorganism is the genus of *Eubacterium*.

7. The microorganism of claim 6, wherein the microorganism is *Eubacterium limosum*.

8. The microorganism of claim 6, wherein the microorganism comprises alsS and alsD genes.

9. The microorganism of claim 6, wherein the microorganism comprises alsS; alsD; and bdh or budC genes.

10. A method for preparing a compound comprising culturing the microorganism of claim 6.

11. The method of claim 10, wherein the compound is selected from acetoin and 2,3-butanediol.

12. A method for removing carbon monoxide gas, comprising culturing a microorganism comprising the acetyl-CoA synthasee variant of claim 1 under gas conditions containing carbon monoxide (CO).

13. A microorganism comprising the acetyl-CoA synthase variant of claim 1, wherein the microorganism is *Eubacterium limosum* KCTC15034BP.

* * * * *

UNITED STATES PATENT AND TRADEMARK OFFICE
CERTIFICATE OF CORRECTION

| | | |
|---|---|---|
| PATENT NO. | : 12,163,170 B2 | Page 1 of 1 |
| APPLICATION NO. | : 18/045822 | |
| DATED | : December 10, 2024 | |
| INVENTOR(S) | : Byung-Kwan Cho et al. | |

It is certified that error appears in the above-identified patent and that said Letters Patent is hereby corrected as shown below:

In the Claims

Claim 12, Column 40, Lines 18-19, delete "acetyl-CoA synthasee" and insert -- acetyl-CoA synthase -- therefor.

Signed and Sealed this
Twenty-eighth Day of January, 2025

Coke Morgan Stewart
*Acting Director of the United States Patent and Trademark Office*

SEQUENCE LISTING

```
Sequence total quantity: 49
SEQ ID NO: 1          moltype = AA  length = 715
FEATURE               Location/Qualifiers
source                1..715
                      mol_type = protein
                      organism = Eubacterium sp.
```

```
SEQUENCE: 1
MERKTYNLFD IIYSGTAKYL ERAEKDVAKA IEEKGRDAEA KLPDTAYGLA TIYAITGEKL    60
LTVGDLERGI EMAKEHINRT NMLADALEAG VAAAMLCEII QACKYLDGNP HPEWVDGALT   120
DAVVRSFGVA LVTQDIPGVA VIIGEHKDPE QLAKTIKSYQ NKGLQTYLVG KCIDQARDQK   180
IKMGVDLRVI PCGYEIEDVI NVVSVAVRAS IMFGNTPAGE WEKHRIYTRD RVFAFVNVFG   240
DWDDKIIAAG ACAIDMGFPA ITETYINEVP TLLLNQPDLT KTDATSLEAR GIKIKVTEID   300
CPVSVSSAFE GERVRKDNMK AEFGGNRTKA WELVHTVELG DIEDHKITVV GPDIDDPQFD   360
GVDVVRIPFG LEIKVAGKAM QSDFESVLER RLHYFLNYIE GSMHVGQRNI CWVRLTKEAF   420
DAGFRLRHFG EVVYAKMLDE FGKVVDKVEV TIYTKEEDVV RLEEELVRPI YNVRDDRLNS   480
LTDESVDVFY TCTLCQSFAP SHVCVVTPER LGLCGAVSWL DSKATKELDP TGPAQPIEKN   540
GVIDERLGAW EEVNDVVAKC SQGAVEKVTL YSILEDPMTS CGCFECICGI MPEANGVVIV   600
NREFGGMTPT GMTFGELASM TGGGVQTPGF MGHGRHFISS KKFMAAEGGI ERIVWMPKEL   660
KDDVAERLNK SVQELYGIEN FTDMVCDETI AVDSEAVLEF LTEKGHPALE MDPIM        715

SEQ ID NO: 2          moltype = DNA  length = 1908
FEATURE               Location/Qualifiers
source                1..1908
                      mol_type = genomic DNA
                      organism = Eubacterium sp.
SEQUENCE: 2
atggaacgta aagacttataa tcttttttgat ataatttaca gtggtactgc taaatatctt    60
gaacgtgctg aaaaagatgt agcaaaggcc attgaagaaa aaggcagaga tgcagaagct   120
aaactgccgg ataccgctta tggcttagcc acaatttacg caatcacagg cgaaaaatta   180
ttaacagtag gcgatctgga acgcggtatt gaaatggcaa agaacacatc aaccgcaca    240
aacatgctgc ctgacgcttt agaagccggt gttgctgctg caatgttatg tgaaattatc   300
caggcctgca aatactagaa cggcaaccca catcccgaat gtagacggg tcgcattgacc   360
gatgcggttg tccgttcttt cggtgttgct ctggttaccc aggatatccc aggtgttgct   420
gttatcatcg gggaacacaa ggatcctgaa cagttagcaa aaacaatcaa atcttatcag   480
aataaaggtc ttcagaccta tctggttggt aaatgtattg accaggcaag agaccagaaa   540
atcaaaatgg gtgttgacct tcgtgttatc ccatgcggtt acgaaatcga agatgttatc   600
aacgttgtat ctgttgctgt acgtgcttct atcatgttcg gtaacacacc agccggcgaa   660
tgggaaaaac acagaatcta cacaagagac cgtgtattcg catttgttaa tgtatttggc   720
gactgggatg acaagatcat cgctgctggc gcctgcgcaa ttgatatggg cttcccggca   780
atcacagaaa cctacattaa tgaagttcct accctgttat taaaccagcc agacctgaca   840
aaaacagacg ctacctctct tgaagcccgt ggcatcaaga tcaaggttac cgaaattgac   900
tgtccggtat ctgtatcctc cgcttttgaa ggcgaacgtg tccgtaaaga caacatgaaa   960
gctgaattcg gtgaaacaga acaaaagcc tgggaattag ttcatactgt agaattaggc  1020
gatatcgaag atcataagat cactgttgtc ggcccggata ttgacgatcc acagtttgac  1080
ggcgttgacg ttgtccgtat cccatttggt ctggaaatta agttgctgga taagcaatg   1140
cagtccgact ttgaatctgt acttgaaaga agttacact acttcttaaa ctacattgaa   1200
ggttcaatgc acgttggaca gagaaatatc tgctgggttc gttaaccaa agaagcattt   1260
gatgctggct tcagactgcg ccacttcggt gaagtagttt acgctaagat gttagacgaa  1320
tttggtaaag tagttgataa agttgaagtt accatctcaa ccaaagaaga agatgttgta  1380
cgtcttgaag aagaactggt tagaccaatc tacaactac gtgatgacag actgaactca   1440
ctgacagatg aaagtgtcga tgtattctac acctgtacac tgtgccagtc ctttgctcct  1500
tctcacgttt gtgttgtaac acctgaacgt ttaggtctct cgcggtgctgt ttcctggtta  1560
gactccaaag caaccaaaga gcttaccca acccgtcacg cacagccaat cgaaaagaat   1620
ggtgttatcg acgaacgctt aggcgcatgg gaagaagtca atgacgttgt tgccaagtgc   1680
tctcagggtg cagttgaaaa agttaccta tactctatcc ttgaagatcc aatgacctcc   1740
tgtggttgct cgaatgtat ctgtggtatt atgccagaag ccaacggtgt tgttattgtt    1800
aaccgtgaat tcggcggcat gacacctact ggtatgacct cggtgaatt agcttccatg   1860
acaggcgggtg gggttcagac tcctggcttc atgggccacg gacgtcac               1908

SEQ ID NO: 3          moltype = AA   length = 715
FEATURE               Location/Qualifiers
source                1..715
                      mol_type = protein
                      organism = synthetic construct
SEQUENCE: 3
MERKTYNLFD IIYSGTAKYL ERAEKDVAKA IEEKGRDAEA KLPDTAYGLA TIYAITGEKL    60
LTVGDLERGI EMAKEHINRT NMLADALEAG VAAAMLCEII QACKYLDGNP HPEWVDGALT   120
DAVVRSFGVA LVTQDIPGVA VIIGEHKDPE QLAKTIKSYQ NKGLQTYLVG KCIDQARDQK   180
IKMGVDLRVI PCGYEIEDVI NVVSVAVRAS IMFGNTPAGE WEKHRIYTRD RVFAFVNVFG   240
DWDDKIIAAG ACAIDMGFPA ITETYINEVP TLLLNQPDLT KTDATSLEAR GIKIKVTEID   300
CPVSVSSAFE GERVRKDNMK AEFGGNRTKA WELVHTVELG DIEDHKITVV GPDIDDPQFD   360
GVDVVRIPFG LEIKVAGKAM QSDFESVLER RLHYFLNYIE GSMHVGQRNI CWVRLTKEAF   420
DAGFRLRHFG EVVYAKMLDE FGKVVDKVEV TIYTKEEDVV RLEEELVRPI YNVRDDRLNS   480
LTDESVDVFY TCTLCQSFAP SHVCVVTPER LGLCGAVSWL DSKATKELDP TGPAQPIEKN   540
GVIDERLGAW EEVNDVVAKC SQGAVEKVTL YSILEDPMTS CGCFECICGI MPEANGVVIV   600
NREFGGMTPT GMTFGELASM TGGGVQTPGF MGHGRRFISS KKFMAAEGGI ERIVWMPKEL   660
KDDVAERLNK SVQELYGIEN FTDMVCDETI AVDSEAVLEF LTEKGHPALE MDPIM        715

SEQ ID NO: 4          moltype = DNA  length = 2148
FEATURE               Location/Qualifiers
source                1..2148
                      mol_type = other DNA
                      organism = synthetic construct
SEQUENCE: 4
atggaacgta aagacttataa tcttttttgat ataatttaca gtggtactgc taaatatctt    60
```

```
gaacgtgctg aaaaagatgt agcaaaggcc attgaagaaa aaggcagaga tgcagaagct    120
aaactgccgg ataccgctta tggcttagcc acaatttacg caatcacagg cgaaaaatta    180
ttaacagtag gcgatctgga acgcggtatt gaaatggcaa agaacacat caaccgcaca     240
aacatgctgg ctgacgcttt agaagccggt gttgctgctg caatgttatg tgaaattatc    300
caggcctgca aatacttaga cggcaaccca catccgaatg gggtagacgg cgcattgacc    360
gatgcggttg tccgttcttt cggtgttgct ctggttaccc aggatatccc aggtgttgct    420
gttatcatcg gggaacacaa ggatcctgaa cagttagcaa aaacaatcaa atcttatcag    480
aataaaggtc ttcagaccta tctggttggt aaatgtattg accaggcaag agaccagaaa    540
atcaaaatgg gtgttgacct tcgtgttatc ccatgcggtt acgaaatcga agatgttatc    600
aacgttgtat ctgttgctgt acgtgcttct atcatgttcg gtaacacacc agccggcgaa    660
tgggaaaaac acagaatcta cacaagagac cgtgtattcg catttgttaa tgtatttggc    720
gactgggatg acaagatcat cgctgctggc gcctgcgcaa ttgatatggg cttcccggca    780
atcacagaaa cctacattaa tgaagttcct accctgttat taaaccagcc agacctgaca    840
aaaacagacg ctacctctct tgaagcccgt ggcatcagaa tcaaggttac cgaaattgac    900
tgtccggtat ctgtatcctc cgcttttcgaa ggcgaacgtg tccgtaaaga caacatgaaa    960
gctgaattcg gtggaaacag aacaaaagcc tgggaattag ttcatactgt agaattaggc   1020
gatatcgaag atcataagat cactgttgtc ggcccggata ttgacgatcc acagtttgac   1080
ggcgttgacg ttgtccgtat cccatttggt ctggaaatta agttgctggt taaagcaatg   1140
cagtccgact ttgaatctgt acttgaaaga agattacact acttcttaaa ctacattgaa   1200
ggttcaatgc acgttggaca gagaaatatc tgctgggttc gttaaccaa agaagcattt    1260
gatgctggct tcagactgcg ccacttcggt gaagtagttt acgctaagat gttagacgaa   1320
tttggtaaag tagttgataa agttgaagtt accatctcaa ccaaagaaga agatgttgta   1380
cgtcttgaag aagaactggt tagaccaatc tacaacgtac gtgatgacag actgaactca   1440
ctgacagatg aaagtgtcga tgtattctac acctgtacac tgtgccagtc ctttgctcct   1500
tctcacgttt gtgttgtaac acctgaacgt ttaggtctct gcggtgctgt ttcctggtta   1560
gactccaaag caaccaaaga gcttgaccca accggtcctg cacagccaat cgaaaagaat   1620
ggtgttatcg acgaacgctt aggcgcatgg gaagaagtca atgacgttgt tgccaagtgc   1680
tctcagggtg cagttgaaaa agttacctta tactctatcc ttgaagatcc aatgacctcc   1740
tgtgttgct tcgaatgtat ctgtggtatt atgccagaag ccaacggtgt tgttattgtt    1800
aaccgtgaat tcggcggcat gacacctact ggtatgacct tcggtgaatt agcttccatg   1860
acaggcggtg gggttcagac tcctggcttc atgggccacg gacgtcgctt catcagctcc   1920
aagaaattta tggctgctga aggtggtatc gaaagaatcg tatggatgcc taaggaattg   1980
aaagacgacg ttgcagaaag attaaacaaa tctgtacagg aattatacgg aattgaaaac   2040
ttcacagaca tggtttgtga tgaaacaatt gctgttgact ccgaagcagt attagaattc   2100
ttaacagaaa aaggccatcc agcactgaa atggatccaa ttatgtaa               2148

SEQ ID NO: 5            moltype = DNA   length = 49
FEATURE                 Location/Qualifiers
source                  1..49
                        mol_type = other DNA
                        organism = synthetic construct
SEQUENCE: 5
ccatgatacg aattcctcga gaagaagtta ataaaaaat aagcccta                 49

SEQ ID NO: 6            moltype = DNA   length = 49
FEATURE                 Location/Qualifiers
source                  1..49
                        mol_type = other DNA
                        organism = synthetic construct
SEQUENCE: 6
ttttattaat ctagaaagct taataattcc tccaaacttt tataattta               49

SEQ ID NO: 7            moltype = DNA   length = 34
FEATURE                 Location/Qualifiers
source                  1..34
                        mol_type = other DNA
                        organism = synthetic construct
SEQUENCE: 7
acgtacgtgt agcaagactg aactcactga caga                               34

SEQ ID NO: 8            moltype = DNA   length = 32
FEATURE                 Location/Qualifiers
source                  1..32
                        mol_type = other DNA
                        organism = synthetic construct
SEQUENCE: 8
cagtcttgct acacgtacgt tgtagattgg tc                                 32

SEQ ID NO: 9            moltype = DNA   length = 39
FEATURE                 Location/Qualifiers
source                  1..39
                        mol_type = other DNA
                        organism = synthetic construct
SEQUENCE: 9
tacgaattcc tcgagaaaga agatttgcta aagaaagag                          39

SEQ ID NO: 10           moltype = DNA   length = 24
FEATURE                 Location/Qualifiers
source                  1..24
```

```
                         mol_type = other DNA
                         organism = synthetic construct
SEQUENCE: 10
gaaaacctct ttcaacgaaa taag                                          24

SEQ ID NO: 11            moltype = DNA  length = 47
FEATURE                  Location/Qualifiers
source                   1..47
                         mol_type = other DNA
                         organism = synthetic construct
SEQUENCE: 11
ttatttcgtt gaaagaggtt ttcaaccatg gtgaaggctg ctctttg                 47

SEQ ID NO: 12            moltype = DNA  length = 40
FEATURE                  Location/Qualifiers
source                   1..40
                         mol_type = other DNA
                         organism = synthetic construct
SEQUENCE: 12
aactcgtctc aaagtcttag gcggccgctc tagattaata                         40

SEQ ID NO: 13            moltype = DNA  length = 47
FEATURE                  Location/Qualifiers
source                   1..47
                         mol_type = other DNA
                         organism = synthetic construct
SEQUENCE: 13
ttatttcgtt gaaagaggtt ttcaaccatg gtgaaggccg cacggtg                 47

SEQ ID NO: 14            moltype = DNA  length = 40
FEATURE                  Location/Qualifiers
source                   1..40
                         mol_type = other DNA
                         organism = synthetic construct
SEQUENCE: 14
tcctggtccg gcccaattag gcggccgctc tagattaata                         40

SEQ ID NO: 15            moltype = DNA  length = 47
FEATURE                  Location/Qualifiers
source                   1..47
                         mol_type = other DNA
                         organism = synthetic construct
SEQUENCE: 15
ttatttcgtt gaaagaggtt ttcaaccatg gtgcgtgcgg cccgttt                 47

SEQ ID NO: 16            moltype = DNA  length = 40
FEATURE                  Location/Qualifiers
source                   1..40
                         mol_type = other DNA
                         organism = synthetic construct
SEQUENCE: 16
cgaccggcaa gggcctgtaa ggcggccgct ctagattaat                         40

SEQ ID NO: 17            moltype = DNA  length = 47
FEATURE                  Location/Qualifiers
source                   1..47
                         mol_type = other DNA
                         organism = synthetic construct
SEQUENCE: 17
ttatttcgtt gaaagaggtt ttcaaccatg gtgaaaggct ttgcgat                 47

SEQ ID NO: 18            moltype = DNA  length = 40
FEATURE                  Location/Qualifiers
source                   1..40
                         mol_type = other DNA
                         organism = synthetic construct
SEQUENCE: 18
ctgtggtcat tctcgcttaa ggcggccgct ctagattaat                         40

SEQ ID NO: 19            moltype = DNA  length = 47
FEATURE                  Location/Qualifiers
source                   1..47
                         mol_type = other DNA
                         organism = synthetic construct
SEQUENCE: 19
ttatttcgtt gaaagaggtt ttcaaccatg gtgtcaaaag tgtcagg                 47

SEQ ID NO: 20            moltype = DNA  length = 40
FEATURE                  Location/Qualifiers
```

```
source                    1..40
                          mol_type = other DNA
                          organism = synthetic construct
SEQUENCE: 20
ggggaatggt gttcaactaa gcggccgctc tagattaata                              40

SEQ ID NO: 21             moltype = DNA  length = 47
FEATURE                   Location/Qualifiers
source                    1..47
                          mol_type = other DNA
                          organism = synthetic construct
SEQUENCE: 21
ttatttcgtt gaaagaggtt ttcaaccatg gtgaaaaagg tggcact                      47

SEQ ID NO: 22             moltype = DNA  length = 40
FEATURE                   Location/Qualifiers
source                    1..40
                          mol_type = other DNA
                          organism = synthetic construct
SEQUENCE: 22
gtggcatggt ctttaattag gcggccgct ctagattaat                               40

SEQ ID NO: 23             moltype = DNA  length = 47
FEATURE                   Location/Qualifiers
source                    1..47
                          mol_type = other DNA
                          organism = synthetic construct
SEQUENCE: 23
ttatttcgtt gaaagaggtt ttcaaccatg gtgaaaaaag tagcgct                      47

SEQ ID NO: 24             moltype = DNA  length = 40
FEATURE                   Location/Qualifiers
source                    1..40
                          mol_type = other DNA
                          organism = synthetic construct
SEQUENCE: 24
ggggaatggt gttcaactaa ggcggccgct ctagattaat                              40

SEQ ID NO: 25             moltype = DNA  length = 47
FEATURE                   Location/Qualifiers
source                    1..47
                          mol_type = other DNA
                          organism = synthetic construct
SEQUENCE: 25
ttatttcgtt gaaagaggtt ttcaaccatg gtggcgattg agaataa                      47

SEQ ID NO: 26             moltype = DNA  length = 40
FEATURE                   Location/Qualifiers
source                    1..40
                          mol_type = other DNA
                          organism = synthetic construct
SEQUENCE: 26
gaggcatcgt ctatcggtaa ggcggccgct ctagattaat                              40

SEQ ID NO: 27             moltype = DNA  length = 47
FEATURE                   Location/Qualifiers
source                    1..47
                          mol_type = other DNA
                          organism = synthetic construct
SEQUENCE: 27
ttatttcgtt gaaagaggtt ttcaaccatg gtgaaagctg tattgtg                      47

SEQ ID NO: 28             moltype = DNA  length = 40
FEATURE                   Location/Qualifiers
source                    1..40
                          mol_type = other DNA
                          organism = synthetic construct
SEQUENCE: 28
ctgacaaatc cttattgtaa gcggccgctc tagattaata                              40

SEQ ID NO: 29             moltype = DNA  length = 25
FEATURE                   Location/Qualifiers
source                    1..25
                          mol_type = other DNA
                          organism = synthetic construct
SEQUENCE: 29
cggagctcgt aattctctat cactg                                              25

SEQ ID NO: 30             moltype = DNA  length = 33
```

```
FEATURE                 Location/Qualifiers
source                  1..33
                        mol_type = other DNA
                        organism = synthetic construct
SEQUENCE: 30
cgagatctat gaacaaagat attatactct atc                              33

SEQ ID NO: 31           moltype = DNA   length = 42
FEATURE                 Location/Qualifiers
source                  1..42
                        mol_type = other DNA
                        organism = synthetic construct
SEQUENCE: 31
tatggaatag aggttaaaaa ccatggtgtt gacaaaagca ac                    42

SEQ ID NO: 32           moltype = DNA   length = 45
FEATURE                 Location/Qualifiers
source                  1..45
                        mol_type = other DNA
                        organism = synthetic construct
SEQUENCE: 32
ccgagctcgc agatctgatt ttatttgatt tatggaatag aggtt                 45

SEQ ID NO: 33           moltype = DNA   length = 28
FEATURE                 Location/Qualifiers
source                  1..28
                        mol_type = other DNA
                        organism = synthetic construct
SEQUENCE: 33
ccgtcgacct agagagcttt cgttttca                                    28

SEQ ID NO: 34           moltype = DNA   length = 47
FEATURE                 Location/Qualifiers
source                  1..47
                        mol_type = other DNA
                        organism = synthetic construct
SEQUENCE: 34
ccgtcgacaa ctaaacgcag gaggtttaca ccatggaaac taatagc               47

SEQ ID NO: 35           moltype = DNA   length = 39
FEATURE                 Location/Qualifiers
source                  1..39
                        mol_type = other DNA
                        organism = synthetic construct
SEQUENCE: 35
gcggctgagg gttagcctgc aggtcactta ctaagaatt                        39

SEQ ID NO: 36           moltype = DNA   length = 48
FEATURE                 Location/Qualifiers
source                  1..48
                        mol_type = other DNA
                        organism = synthetic construct
SEQUENCE: 36
atgattacga attcgagctc ctagagagct ttcgttttca tgagttcc              48

SEQ ID NO: 37           moltype = DNA   length = 54
FEATURE                 Location/Qualifiers
source                  1..54
                        mol_type = other DNA
                        organism = synthetic construct
SEQUENCE: 37
ttgtttcaag gaggaactcg agatgttgac aaaagcaaca aaagaacaaa aatc       54

SEQ ID NO: 38           moltype = DNA   length = 48
FEATURE                 Location/Qualifiers
source                  1..48
                        mol_type = other DNA
                        organism = synthetic construct
SEQUENCE: 38
gacgttctga gctctcttat tattatacca catttcggct gagcctaa              48

SEQ ID NO: 39           moltype = DNA   length = 45
FEATURE                 Location/Qualifiers
source                  1..45
                        mol_type = other DNA
                        organism = synthetic construct
SEQUENCE: 39
cgagttcctc cttgaaacaa gacgttctga gctctcttat tatta                 45
```

```
SEQ ID NO: 40            moltype = DNA  length = 37
FEATURE                  Location/Qualifiers
source                   1..37
                         mol_type = other DNA
                         organism = synthetic construct
SEQUENCE: 40
ccggtaaatg ggatccatga aggagggcat cttcgtg                              37

SEQ ID NO: 41            moltype = DNA  length = 33
FEATURE                  Location/Qualifiers
source                   1..33
                         mol_type = other DNA
                         organism = synthetic construct
SEQUENCE: 41
acatctcgag ggatcccatt taccgggcca agc                                  33

SEQ ID NO: 42            moltype = DNA  length = 43
FEATURE                  Location/Qualifiers
source                   1..43
                         mol_type = other DNA
                         organism = synthetic construct
SEQUENCE: 42
ttgtcaacat ctcgagttcc tccttgaaac aagacgttct gag                       43

SEQ ID NO: 43            moltype = DNA  length = 48
FEATURE                  Location/Qualifiers
source                   1..48
                         mol_type = other DNA
                         organism = synthetic construct
SEQUENCE: 43
cggtacccgg ggatccacgc gtatggaaac taatagctcg tgcgattg                  48

SEQ ID NO: 44            moltype = DNA  length = 39
FEATURE                  Location/Qualifiers
source                   1..39
                         mol_type = other DNA
                         organism = synthetic construct
SEQUENCE: 44
atgcctgcag gtcgacctaa ccctcagccg cacggatag                            39

SEQ ID NO: 45            moltype = DNA  length = 36
FEATURE                  Location/Qualifiers
source                   1..36
                         mol_type = other DNA
                         organism = synthetic construct
SEQUENCE: 45
gtcacttact aagaattcgc aagaccgatc gggccc                               36

SEQ ID NO: 46            moltype = DNA  length = 41
FEATURE                  Location/Qualifiers
source                   1..41
                         mol_type = other DNA
                         organism = synthetic construct
SEQUENCE: 46
tagcaaatct tctttctcga gggtcatagc tgtttcctga t                         41

SEQ ID NO: 47            moltype = DNA  length = 33
FEATURE                  Location/Qualifiers
source                   1..33
                         mol_type = other DNA
                         organism = synthetic construct
SEQUENCE: 47
aggtcgacgt cacttactaa gaattcgcaa gac                                  33

SEQ ID NO: 48            moltype = DNA  length = 36
FEATURE                  Location/Qualifiers
source                   1..36
                         mol_type = other DNA
                         organism = synthetic construct
SEQUENCE: 48
aggtcgacat gcggatccta aataaaaata agaagc                               36

SEQ ID NO: 49            moltype = DNA  length = 21
FEATURE                  Location/Qualifiers
source                   1..21
                         mol_type = other DNA
                         organism = synthetic construct
```

```
SEQUENCE: 49
ttaggcggcc gctctagatt a                                              21
```